United States Patent [19]

O'Neill

[11] Patent Number: 5,604,252
[45] Date of Patent: Feb. 18, 1997

[54] AZANORBORNANE DERIVATIVES

[75] Inventor: Brian T. O'Neill, Westbrook, Conn.

[73] Assignee: Pfizer Inc., New York, N.Y.

[21] Appl. No.: 167,851

[22] PCT Filed: Jun. 11, 1992

[86] PCT No.: PCT/US92/04697

§ 371 Date: Dec. 14, 1993

§ 102(e) Date: Dec. 14, 1993

[87] PCT Pub. No.: WO93/00330

PCT Pub. Date: Jan. 7, 1993

Related U.S. Application Data

[63] Continuation-in-part of Ser. No. 719,889, Jun. 21, 1991, abandoned.

[51] Int. Cl.$^6$ ............ C07D 487/04; C07D 207/14; A61K 31/40
[52] U.S. Cl. ............ 514/413; 514/426; 548/453; 548/557
[58] Field of Search .................. 548/453, 557; 514/413, 426

[56] References Cited

U.S. PATENT DOCUMENTS 4,925,867  5/1990  Baker et al. .................. 514/425

FOREIGN PATENT DOCUMENTS

| WO90/05729 | 5/1990 | WIPO . |
| WO91/09844 | 7/1991 | WIPO . |
| WO91/18899 | 12/1991 | WIPO . |
| WO92/01688 | 2/1992 | WIPO . |
| WO92/06079 | 4/1992 | WIPO . |

OTHER PUBLICATIONS

Aldrich, "Classes of Compounds and Numerical Cross Reference List," Supplement to the 1984 –1985 Aldrich Catalog/Handbook of Fine Chemicals® 1984 by Aldrich Chemical Company, Inc. of Milwaukee, Wisconsin 53201 (U.S.A.); and .
W. E. Smith in the *Journal of Organic Chemistry*, vol. 37, No. 24, p. 3972 (1972).
Thorbek et al., *Acta Chem. Scand. Ser. B*, B35 (7), 3557–70 (1981).
Warawa et al., *J. Med. Chem.*, 18 (6), 587–593 (1975).
Warawa et al., *J. Med. Chem.*, 17(5), 497–501 (1974).
Warawa et al.. *J. Med. Chem.*, 18 (1), 71–74 (1975).

*Primary Examiner*—David B. Springer
*Attorney, Agent, or Firm*—Peter C. Richardson; Paul H. Ginsburg; Karen Debenedictis

[57] ABSTRACT

The present invention relates to novel azanorbornane derivatives having the formula

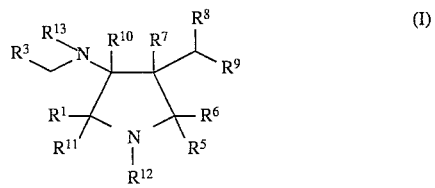

wherein $R^1$ through $R^{12}$ are defined as below, and to novel intermediates used in their synthesis. The compounds having formula I are useful in the treatment of inflammatory and central nervous system disorders, as well as other disorders.

12 Claims, No Drawings

AZANORBORNANE DERIVATIVES

This application is A371 of PCT/US92/04697 filed Jun. 11, 1992 a continuation-in-part of U.S. application Ser. No. 07/719,884, which was filed on Jun. 21, 1991, now abandoned.

BACKGROUND OF THE INVENTION

The present invention relates to novel azanorbornane derivatives and related compounds, pharmaceutical compositions comprising such compounds and the use of such compounds in the treatment and prevention of inflammatory and central nervous system disorders, as well as several other disorders. The pharmaceutically active compounds of this invention are substance P antagonists. This invention also relates to novel intermediates used in the synthesis of such substance P antagonists.

Substance P is a naturally occurring undecapeptide belonging to the tachykinin family of peptides, the latter being named because of their prompt stimulatory action on smooth muscle tissue. More specifically, substance P is a pharmacologically active neuropeptide that is produced in mammals (having originally been isolated from gut) and possesses a characteristic amino acid sequence that is illustrated by D. F. Veber et al. in U.S. Pat. No. 4,680,283. The wide involvement of substance P and other tachykinins in the pathophysiology of numerous diseases has been amply demonstrated in the art. For instance, substance P has recently been shown to be involved in the transmission of pain or migraine (see B. E. B. Sandberg et al., *Journal of Medicinal Chemistry*, 25, 1009 (1982)), as well as in central nervous system disorders such as anxiety and schizophrenia, in respiratory and inflammatory diseases such as asthma and rheumatoid arthritis, respectively, in rheumatic diseases such as fibrositis, and in gastrointestinal disorders and diseases of the GI tract such as ulcerative colitis and Crohn's disease, etc. (see D. Regoli in "Trends in Cluster Headache," edited by F. Sicuteri et al., Elsevier Scientific Publishers, Amsterdam, pp. 85–95 (1987)).

In the recent past, some attempts have been made to provide antagonists for substance P and other tachykinin peptides in order to more effectively treat the various disorders and diseases listed above. The few such antagonists thus far described are generally peptide-like in nature and are therefore too labile from a metabolic point of view to serve as practical therapeutic agents in the treatment of disease. The non-peptidic antagonists of the present invention, on the other hand, do not possess this drawback, being far more stable from a metabolic point of view than the agents referred to above.

Quinuclidine derivatives and related compounds that exhibit activity as substance P receptor antagonists are referred to in PCT Patent Application PCT/US 89/05338, filed Nov. 20, 1989 and U.S. patent application Ser. No. 557,442, filed Jul. 23, 1990, both of which are assigned in common with the present application. Similar compounds are referred to in PCT patent applications entitled "3-Amino-2-Aryl Quinuclidines" and "Quinuclidine Derivatives" and filed on Apr. 25, 1991 and May 15, 1991, respectively. These applications are also assigned in common with the present application.

Piperidine derivatives and related heterocyclic nitrogen containing compounds that are useful as substance P receptor antagonists are referred to in U.S. patent application Ser. No. 619,361, filed Nov. 28, 1990 and U.S. patent application Ser. No. 590,423, filed Sep. 28, 1990, both of which are assigned in common with the present application.

SUMMARY OF THE INVENTION

This invention relates to compounds having the formula

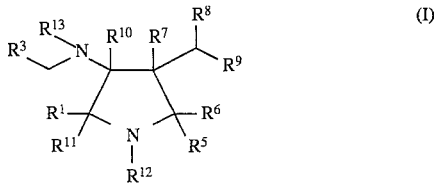

wherein $R^1$ is selected from hydrogen, $(C_1-C_6)$ straight or branched alkyl, $(C_3-C_7)$ cycloalkyl wherein one of the carbon atoms may optionally be replaced by nitrogen, oxygen or sulfur; aryl selected from phenyl, biphenyl, indanyl and naphthyl; heteroaryl selected from thienyl, furyl, pyridyl, thiazolyl, isothiazolyl, oxazolyl, isoxazolyl, triazolyl, tetrazolyl and quinolyl; phenyl $(C_2-C_6)$ alkyl, benzhydryl and benzyl, wherein each of said aryl and heteroaryl groups and the phenyl moieties of said benzyl, phenyl $(C_2-C_6)$ alkyl and benzhydryl may optionally be substituted with one or more substituents independently selected from halo, nitro, $(C_1-C_6)$ alkyl optionally substituted with from one to three fluorine atoms, $(C_1-C_6)$ alkoxy, amino, trihaloalkoxy (e.g., trifluoromethoxy),

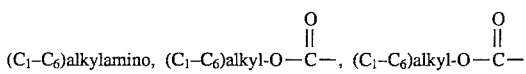

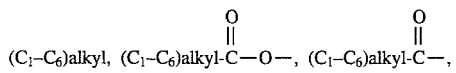

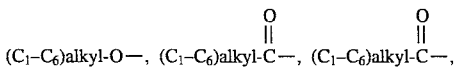

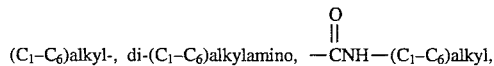

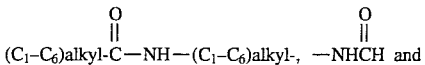

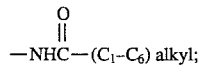

and wherein one of the phenyl moieties of said benzhydryl may optionally be replaced by naphthyl, thienyl, furyl or pyridyl;

$R^3$ is aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; and cycloalkyl having 3 to 7 carbon atoms wherein one of said carbon atoms may optionally be replaced by nitrogen, oxygen or sulfur; wherein each of said aryl and heteroaryl groups may optionally be substituted with one or more substituents, and said $(C_3-C_7)$ cycloalkyl may optionally be substituted with one or two substituents, each of said substituents being independently selected from halo, nitro, $(C_1-C_6)$ alkyl optionally substituted with from one to three fluorine atoms, $(C_1-C_6)$ alkoxy, amino, phenyl, trihaloalkoxy ( e.g., trifluoromethoxy),

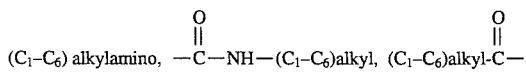

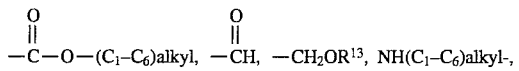

-continued

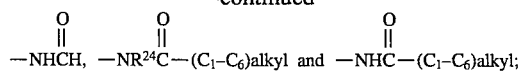

one of $R^5$ and $R^6$ is hydrogen and the other is selected from hydroxymethyl, hydrogen, $(C_1-C_3)$alkyl, $(C_1-C_8)$acyloxy-$(C_1-C_3)$alkyl, $(C_1-C_8)$alkoxymethyl and benzyloxymethyl;

$R^7$ and $R^8$ are independently selected from hydrogen, $(C_1-C_3)$alkyl and phenyl;

$R^9$ is selected from methyl, hydroxymethyl,

$R^{14}R^{15}NCO_2CH_2$—, $R^{16}OCO_2CH_2$—, $(C_1-C_4)$alkyl-$CO_2CH_2$—, —$CONR^{17}R^{18}$, $R^{17}R^{18}NCO_2$—, $R^{19}OCO_2$—, $C_6H_5CH_2CO_2CH_2$—, $C_6H_5CO_2CH_2$—, $(C_1-C_4)$alkyl-$CH(OH)$—, $C_6H_5CH(OH)$—, $C_6H_5CH_2CH(OH)$—, $CH_2$halo, $R^{20}SO_2OCH_2$, —$CO_2R^{16}$ and $R^{21}CO_2$—;

$R^{10}$ and $R^{11}$ are independently selected from hydrogen, $(C_1-C_3)$ alkyl and phenyl;

$R^{12}$ is hydrogen, benzyl or a group of the formula

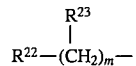

wherein m is an integer from zero to twelve, and any one of the carbon-carbon single bonds of $(CH_2)_m$ may optionally be replaced by a carbon-carbon double or triple bond, and any one of the carbon atoms of $(CH_2)_m$ may optionally be substituted with R23 (as indicated by the slanted line to $R^{23}$ which intersects the horizontal line to $(CH_2)_m$ in the above figure);

$R^{13}$, $R^{14}$, $R^{15}$, $R^{16}$, $R^{17}$, $R^{18}$, $R^{19}$, $R^{20}$, $R^{21}$ and $R^{24}$ are independently selected from hydrogen, $(C_1-C_3)$alkyl and phenyl;

$R^{22}$ and $R^{23}$ are independently selected from hydrogen, hydroxy, halo, amino, carboxy, carboxy$(C_1-C_6)$alkyl, $(C_1-C_6)$alkylamino, di-$(C_1-C_6)$alkylamino, $(C_1-C_6)$alkoxy,

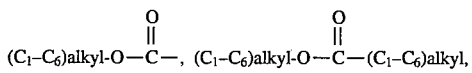

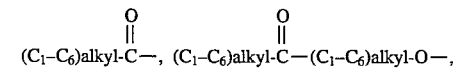

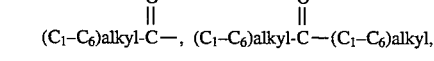

$(C_1-C_6)$straight or branched alkyl, $(C_3-C_7)$ cycloalkyl wherein one of the carbon atoms may optionally be replaced by nitrogen, oxygen or sulfur; aryl selected from phenyl and naphthyl; heteroaryl selected from indanyl, thienyl, furyl, pyridyl, thiazolyl, isothiazolyl, oxazolyl, isoxazolyl, triazolyl, tetrazolyl and quinolyl; phenyl-$(C_2-C_6)$alkyl, benzhydryl and benzyl, wherein each of said aryl and heteroaryl groups and the phenyl moieties of said benzyl, phenyl-$(C_2-C_6)$alkyl and benzhydryl may optionally be substituted with one or two substituents independently selected from halo, nitro, $(C_1-C_6)$alkyl optionally substituted with from one to three fluorine atoms, $(C_1-C_6)$alkoxy optionally substituted with from one to three fluorine atoms, trifluoromethyl, amino, $(C_1-C_6)$-alkylamino,

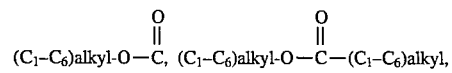

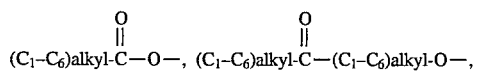

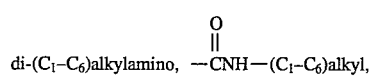

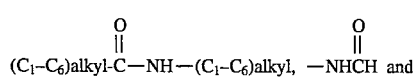

and wherein one of the phenyl moieties of said benzhydryl may optionally be replaced by naphthyl, thienyl, furyl or pyridyl;

or $R^9$, together with the carbon to which it is attached, the nitrogen of the pyrrolidine ring, the carbon to which $R^7$ is attached and the carbon to which $R^5$ and $R^6$ are attached form a second pyrrolidine ring; with the proviso that when $R^9$, together with the carbon to which it is attached, the nitrogen of the pyrrolidine ring, the carbon to which $R^7$ is attached and the carbon to which $R^5$ and $R^6$ are attached, form a second pyrrolidine ring (thus forming a bicyclic structure containing a bridgehead nitrogen), either $R^{12}$ is absent or $R^{12}$ is present and the nitrogen of the second pyrrolidine ring is positively charged.

Compounds of the formula I that contain two pyrrolidine rings may be represented by one of the following two structures, depending on whether $R^{12}$ is present or absent.

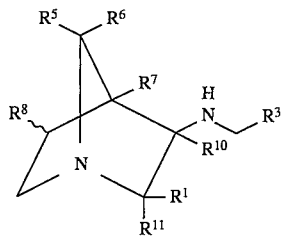

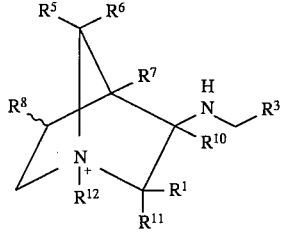

wherein R is selected from hydrogen, $(C_1-C_4)$alkyl, phenyl or benzyl.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to compounds of the formula

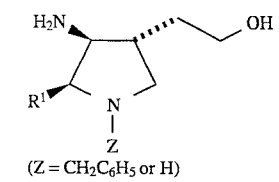

II (Z = CH₂C₆H₅ or H)

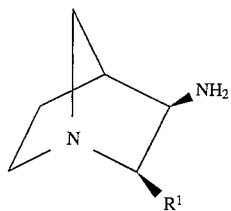

III

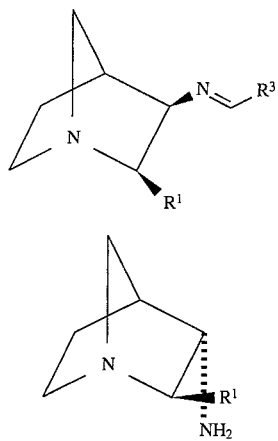

IV

V

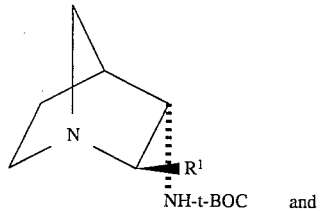

VI

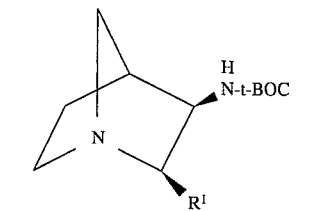

XV wherein $R^1$ is defined as for formula I and t-Boc is t-butyloxycarbonyl.

The term "halo" as used herein unless otherwise indicated, includes chloro, fluoro, bromo and iodo.

The term "alkyl", as used herein, unless otherwise indicated, includes saturated monovalent hydrocarbon radicals having straight, branched or cyclic moieties or combinations thereof.

Preferred compounds of the formula I are those wherein $R^1$ is benzhydryl.

Other preferred compounds of the formula I are those wherein $R^1$ is diphenylmethyl, $R^3$ is aryl selected from phenyl or indanyl wherein each of said aryl groups may be optionally substituted with one, two or three substituents, each of $R^5$, $R^6$, $R^7$, $R^8$, $R^{10}$, and $R^{11}$ is hydrogen, $R^9$ is selected from hydroxymethyl, methoxymethyl, —$CO_2R^{16}$, —$CONR^{17}R^{18}$, $R^{14}R^{15}NCO_2CH_2$—, $R^{16}OCO_2CH_2$—, ($C_1$-$C_4$)alkyl-$CO_2CH_2$—, $C_6H_5CH_2CO_2CH_2$—, —$CH_2$halo and $R^{20}SO_2OCH_2$—, and $R^{12}$ is hydrogen or benzyl.

Other preferred compounds of formula I are those wherein $R^1$ is phenyl, $R^3$ is aryl selected from phenyl or indanyl wherein each of said aryl groups may be optionally substituted with one, two or three substituents, each of $R^5$, $R^6$, $R^7$, $R^8$, $R^{10}$, and $R^{11}$ is hydrogen, $R^9$ is selected from hydroxymethyl, methoxymethyl, —$CO_2R^{18}$, —$CONR^{17}R^{18}$, $R^{14}R^{15}NCO_2CH_2CH_2$—, $R^{16}OCO_2CH_2$—, ($C_1$-$C_4$) alkyl-$CO_2CH_2$—, —$CH_2$halo, $R^{20}SO_2OCH$—, and $R^{12}$ is hydrogen or benzyl.

Other preferred compounds of the formula I are those wherein $R^1$ is diphenylmethyl, $R^3$ is aryl selected from phenyl or indanyl wherein each of said aryl groups; may be optionally substituted with one, two or three substituents, each of $R^5$, $R^6$, $R^7$, $R^8$, $R^{10}$, $R^{11}$ and $R^{13}$ is hydrogen, and wherein $R^9$, together carbon to which it is attached, the nitrogen of the pyrrolidine ring, the carbon to which $R^7$ is attached and the carbon to which $R^5$ and $R^6$ are attached, form a second pyrrolidine ring (thus forming a bicyclic structure containing a bridgehead nitrogen).

Specific preferred compounds of the formula I include the following:

(2S, 3S, 4R)-2-diphenylmethyl-3-[(2-methoxy-4,5-dimethylphenyl)methylamino]-4-(2-hydroxyethyl)pyrrolidine;

(2SR, 3SR, 4RS)-2-diphenylmethyl-3-[(2-methoxy-4,5-dimethylphenyl)methylamino]-4-(2-hydroxyethyl)pyrrolidine;

(2SR, 3SR, 4RS)-2-diphenylmethyl-3-[(2-methoxy-5-(methylethyl)phenyl)methylamino]-4-(carbomethoxymethyl)pyrrolidine;

(2SR, 3SR, 4RS)-2-diphenylmethyl-3-[(2-methoxy-5-(methylethyl)phenyl)methylamino]-4-(carboxymethyl)pyrrolidine;

(2SR, 3SR, 4RS)-2-diphenylmethyl-3-[(2-methoxy-5-(methylethyl)phenyl)methylamino]-4-(2-dimethylaminocarbamoylethyl)pyrrolidine;

(2SR, 3SR, 4RS)-2-diphenylmethyl-3-[(2-trifluoromethoxyphenyl)methylamino]-4-(2-hydroxyethyl)pyrrolidine;

(2S, 3S, 4R)-2-diphenylmethyl-3-[(2-methoxy-5-(1,1-dimethylethyl)phenyl)methylamino]-4-(2-hydroxyethyl)pyrrolidine;

(2SR, 3SR, 4RS)-2-diphenylmethyl-3-[(2-methoxy-5-(1,1-dimethylethyl)phenyl)methylamino]-4-(2-methoxyethyl)pyrrolidine;

(2S, 3S, 4R)-2-diphenylmethyl-3-[(2-methoxy-5-methylethyl)phenyl)methylamino]-4-(2-hydroxyethyl)pyrrolidine;

(2SR, 3SR, 4RS)-2-diphenylmethyl-3-[(2-methoxy-5-methylethyl)phenyl)methylamino]-4-(2-methoxyethyl)pyrrolidine;

(2SR, 3SR, 4RS)-2-diphenylmethyl-3-[(2-methyl-5-(1,1-dimethylethyl)phenyl)methylamino]-4-(2-hydroxyethyl)pyrrolidine;

(1SR, 2SR, 3SR, 4RS)-1-aza-2-diphenylmethyl-3-[(2-methoxy-4,5-dimethylphenyl)-methylamino]bicyclo-[2.2.1]heptane;

(1SR, 2SR, 3SR, 4RS)-1-aza-2-diphenylmethyl-3-[(2-methoxyphenyl)methylamino]bicyclo[2.2.1]heptane;

(1SR, 2SR, 3SR, 4RS)-1-aza-2-diphenylmethyl-3-[(2-methoxy-5-(1,1-dimethylethyl)phenyl)methylamino]bicyclo-[2.2.1]heptane;

(1SR, 2SR, 3SR, 4RS)-1-aza-2-diphenylmethyl-3-[(2-methoxy-5-trifluoromethoxyphenyl)methylamino]bicyclo-[2.2.1]heptane;

(1SR, 2SR, 3SR, 4RS)-1-aza-2-diphenylmethyl-3-[(2-methoxy-5-(1-methylethyl)phenyl)methylamino]bicyclo[2.2.1]heptane;

(1SR, 2SR, 3SR, 4RS)-1-aza-2-diphenylmethyl-3-[(2-methoxy-5-propylphenyl)methylamino]bicyclo[2.2.1]heptane;

(1SR, 2SR, 3SR, 4RS)-1-aza-2-diphenylmethyl-3-[(2-methoxy-5-(1-methylpropyl)phenyl)methylamino]bicyclo[2.2.1]heptane;

(1SR, 2SR, 3SR, 4RS)-1-aza-2-phenyl-3-[(2-methoxyphenyl)methylamino]bicyclo[2.2.1]heptane;

(1SR, 2SR, 3RS, 4RS)-1-aza-2-phenyl-3-[(2-methoxy-5-trifluoromethoxyphenyl)methylamino]bicyclo[2.2.1]heptane;

(2SR, 3SR, 4RS)-N-1-phenylmethyl-2-diphenylmethyl-3-[(2-methoxyphenyl)methylamino]-4-(2-hydroxyethyl)pyrrolidine;

(2SR, 3SR, 4RS)-2-diphenylmethyl-3-[(2-methoxyphenyl)methylamino]-4-(2-hydroxyethyl)pyrrolidine;

(2SR, 3SR, 4RS)-2-diphenylmethyl-3-[(2-methoxy-5-(1,1-dimethylethyl)phenyl)methylamino]-4-(2-hydroxyethyl)pyrrolidine;

(2SR, 3SR, 4RS)-2-diphenylmethyl-3-[(2-methoxy-5-trifluoromethoxyphenyl)methylamino]-4-(2-hydroxyethyl)pyrrolidine;

(2SR, 3SR, 4RS)-2-diphenylmethyl-3-[(2-methoxy-5-(1-methylethyl)phenyl)methy-1-amino]-4-(2-hydroxyethyl)pyrrolidine;

(2SR, 3SR, 4RS)-2-diphenylmethyl-3-[(2-methoxy-5-propylphenyl)methylamino]-4-(2-hydroxyethyl)pyrrolidine;

(2SR, 3SR, 4RS)-2-diphenylmethyl-3-[(2-methoxy-5-(1-methyl-1-propyl)phenyl)methylamino]-4-(2-hydroxyethyl)pyrrolidine;

(2SR, 3SR, 4RS)-2-diphenylmethyl-3-[(2-trifluoromethoxy-5-(1,1-dimethylethyl)phenyl)methylamino]-4-(2-hydroxyethyl)pyrrolidine;

(2SR, 3SR, 4RS)-2-diphenylmethyl-3-[(2-methoxy-5-chlorophenyl)methylanino]-4-(2-hydroxyethyl)pyrrolidine;

(2SR, 3SR, 4RS)-2-phenyl-3-[(2-methoxyphenyl)methylamino]-4- (2-hydroxyethyl)pyrrolidine;

(2SR, 3SR, 4RS)-2-phenyl-3-[(2-methoxy-5-(1,1-dimethylethyl)phenyl)methylamino]-4-(2-hydroxyethyl)pyrrolidine; and (2SR, 3SR, 4RS)-2-phenyl-3-[(2-methoxy-5-trifluoromethoxyphenyl)methylamino]-4-(2-hydroxyethyl)pyrrolidine.

Other compounds of the formula I include:

1-aza-2-diphenylmethyl-3-(phenylmethylamino)bicyclo[2.2.1]heptane;

1-aza-2-diphenylmethyl-3-[(2-trifluoromethylphenyl)methylamino]bicyclo[2.2.1]heptane;

1-aza-2-diphenylmethyl-3-[(2-chlorophenyl)methylamino]bicyclo[2.2.1]heptane;

1-aza-2-diphenylmethyl-3-[(2-methylphenyl)methylamino]bicyclo[2.2.1]heptane;

1-aza-2-diphenylmethyl-3-[(2-methoxyphenyl)methylamino]bicyclo[2.2.1]heptane;

1-aza-2-diphenylmethyl-3-[(2-methoxy-5-methylphenyl)methylamino]bicyclo[2.2.1]heptane;

1-aza-2-diphenylmethyl-3-[(2-methoxy-5-(1,1-dimethylethyl)phenyl)methylamino]bicyclo[2.2.1]heptane;

1-aza-2-diphenylmethyl-3-[(2-methoxy-5-trifluoromethoxyphenyl)methylamino]bicyclo[2.2.1]heptane;

1-aza-2-diphenylmethyl-3-[(2-methoxy-5-(1-methylethyl)phenyl)methylamino]bicyclo[2.2.1]heptane;

1-aza-2-diphenylmethyl-3-[(2-methoxy-5-ethylphenyl)methylamino]bicyclo[2.2.1]heptane;

1-aza-2-diphenylmethyl-3-[(2-methoxy-5-phenylphenyl)methylamino]bicyclo[2.2.1]heptane;

1-aza-2-diphenylmethyl-3-[(2-methoxy-5-propylphenyl)methylamino]bicyclo[2.2.1]heptane;

1-aza-2-diphenylmethyl-3-[(2-methoxy-5-butylphenyl)methylamino]bicyclo[2.2.1]heptane;

1-aza-2-diphenylmethyl-3-[(2-methoxy-5-(1-methylpropyl)phenyl)methylamino]bicyclo[2.2.1]heptane;

1-aza-2-diphenylmethyl-3-[(2-methoxy-5-trifluoromethylphenyl)methylamino]bicyclo[2.2.1]heptane;

1-aza-2-diphenylmethyl-3-[(2-methoxy-5-chlorophenyl)methylamino]bicyclo[2.2.1]heptane;

1-aza-2-diphenylmethyl-3-[(2-methoxy-5-fluorophenyl)methylamino]bicyclo[2.2.1]heptane;

1-aza-2-diphenylmethyl-3-[(2-methoxy-5-methoxyphenyl)methylamino]bicyclo[2.2.1]heptane;

1-aza-2-diphenylmethyl-3-[(2-methoxy-5-phenoxylphenyl)methylamino]bicyclo[2.2.1]heptane;

1-aza-2-diphenylmethyl-3-[(2-methoxy-5-(N,N-dimethylamino)phenyl)methylamino]bicyclo[2.2.1]heptane;

1-aza-2-diphenylmethyl-3-[(2-methoxy-5-hydroxymethylphenyl)methylamino]bicyclo[2.2.1]heptane;

1-aza-2-diphenylmethyl-3-[(2-methoxy-5-nitrophenyl)methylamino]bicyclo[2.2.1]heptane;

1-aza-2-diphenylmethyl-3-[(2-methoxyphenyl)methylamino]-7-hydroxymethylbicyclo[2.2.1]heptane;

1-aza-2-diphenylmethyl-3-[(2-methoxyphenyl)methylamino]-7-methoxymethylbicyclo[2.2.1]heptane;

1-aza-2-diphenylmethyl-3-[(2-methoxy-3-pyridyl)methylamino]bicyclo[2.2.1]heptane;

1-aza-2-phenyl-3-[(2-methoxyphenyl)methylamino]bicyclo[2.2.1]heptane;

1-aza-2-phenyl-3-[(2-methoxy-5-(1,1-dimethylethyl)phenyl)methylamino]bicyclo[2.2.1]heptane;

1-aza-2-phenyl-3-[(2-methoxy-5-trifluoromethoxyphenyl)methylamino]bicyclo[2.2.1]heptane;

1-aza-2-phenyl-3-[(2-methoxy-5-chlorophenyl)methylamino]bicyclo[2.2.1]heptane;

2-diphenylmethyl-3-(phenylmethylamino)-4-(2-hydroxyethyl)pyrrolidine;

2-diphenylmethyl-3-[(2-trifluoromethylphenyl)methylamino]-4-(2-hydroxyethyl)pyrrolidine;

2-diphenylmethyl-3-[(2-chlorophenyl)methylamino]-4-(2-hydroxyethyl)pyrrolidine;

2-diphenylmethyl-3-[(2-methylphenyl)methylamino]-4-(2-hydroxyethyl)pyrrolidine;

N-1-phenylmethyl-2-diphenylmethyl-3-[(2-methoxyphenyl)methylamino]-4-(2-hydroxyethyl)pyrrolidine;

2-diphenylmethyl-3-[(2-methoxyphenyl)methylamino]-4-(2hydroxyethyl)pyrrolidine;

2-diphenylmethyl-3-[(2-methoxy-5-methylphenyl)methylamino]-4-(2-hydroxyethyl)pyrrolidine;

2-diphenylmethyl-3-[(2-methoxy-5-(1,1-dimethylethyl)phenyl)methylamino]-4-(2-hydroxyethyl)pyrrolidine;

2-diphenylmethyl-3-[(2-methoxy-5-trifluoromethoxyphenyl)methylamino]-4-(2-hydroxyethyl)pyrrolidine;

2-diphenylmethyl-3-[(2-methoxy-5-(1-methylethyl)phenyl)methylamino]-4-(2-hydroxyethyl)pyrrolidine;

2-diphenylmethyl-3-[(2-methoxy-5-ethylphenyl)methylamino]-4-(2-hydroxyethyl)pyrrolidine;

2-diphenylmethyl-3-[(2-methoxy-5-phenylphenyl)methylamino]-4-(2-hydroxyethyl)pyrrolidine;

2-diphenylmethyl-3-[(2-methoxy-5-propylphenyl)methylamino]-4-(2-hydroxyethyl)pyrrolidine;

2-diphenylmethyl-3-[(2-methoxy-5-butylphenyl)methylamino]-4-(2-hydroxyethyl)pyrrolidine;

2-diphenylmethyl-3-[(2-methoxy-5-(1-methylpropyl)phenol)methylamino]-4-(2-hydroxyethyl)pyrrolidine;

2-diphenylmethyl-3-[(2-methoxy-5-trifluoromethylphenyl)methylamino]-4-(2-hydroxyethyl)pyrrolidine;
2-diphenylmethyl-3-[(2-methoxy-5-chlorophenyl)methylamino]-4-(2-hydroxyethyl)pyrrolidine;
2-diphenylmethyl-3-[(2-methoxy-5-fluorophenyl)methylamino]-4-(2-hydroxyethyl)pyrrolidine;
2-diphenylmethyl-3-[(2-methoxy-5-methoxyphenyl)methylamino]-4-(2-hydroxyethyl)pyrrolidine;
2-diphenylmethyl-3-[(2-methoxy-5-phenoxyphenyl)methylamino]-4-(2-hydroxyethyl)pyrrolidine;
2-diphenylmethyl-3-[(2-methoxy-5-(N,N-dimethylamino)phenyl)methylamino]-4-(2-hydroxyethyl)pyrrolidine;
2-diphenylmethyl-3-[(2-methoxy-5-hydroxymethylphenyl)methylamino]-4-(2-hydroxyethyl)pyrrolidine;
2-diphenylmethyl-3-[(2-methoxy-5-nitrophenyl)methylamino]-4-(2-hydroxyethyl)pyrrolidine;
2-diphenylmethyl-3-[(2-methoxyphenyl)methylamino]-4-(2-hydroxyethyl)-5-hydroxymethylpyrrolidine;
2-diphenylmethyl-3-[(2-methoxyphenyl)methylamino]-4-(2-hydroxyethyl)-5-methoxymethylpyrrolidine;
2-diphenylmethyl-3-[(2-methoxy-3-pyridyl)methylamino]-4-(2-hydroxyethyl)pyrrolidine;
2-phenyl-3-(phenylmethylamino)-4-(2-hydroxyethyl)pyrrolidine;
2-phenyl-3-[(2-trifluoromethylphenyl)methylamino]-4-(2-hydroxyethyl)pyrrolidine;
2-phenyl-3-[(2-chlorophenyl)methylamino]-4-(2-hydroxyethyl)pyrrolidine;
2-phenyl-3-[(2-methylphenyl)methylamino]-4-(2-hydroxyethyl)pyrrolidine;
2-phenyl-3-[(2-methoxyphenyl)methylamino]-4-(2-hydroxyethyl)pyrrolidine;
2-phenyl-3-[(2-methoxy-5-methylphenyl)methylamino]-4-(2-hydroxyethyl)pyrrolidine;
2-phenyl-3-[(2-methoxy-5-(1,1-dimethylethyl)phenyl)methylamino]-4-(2-hydroxyethyl)pyrrolidine;
2-phenyl-3-[(2-methoxy-5-trifluoromethoxyphenyl)methylamino]-4-(2-hydroxyethyl)pyrrolidine;
2-phenyl-3-[(2-methoxy-5-(1-methylethyl)phenyl)methylamino]-4-(2-hydroxyethyl)pyrrolidine;
2-phenyl-3-[(2-methoxy-5-ethylphenyl)methylamino]-4-(2-hydroxyethyl)pyrrolidine;
2-phenyl-3-[(2-methoxy-5-phenylphenyl)methylamino]-4-(2-hydroxyethyl)pyrrolidine;
2-phenyl-3-[(2-methoxy-5-propylphenyl)methylamino]-4-(2-hydroxyethyl)pyrrolidine;
2-phenyl-3-[(2-methoxy-5-butylphenyl)methylamino]-4-(2-hydroxyethyl)pyrrolidine;
2-phenyl-3-[(2-methoxy-5-(1-methylpropyl)phenyl)methylamino]-4-(2-hydroxyethyl)pyrrolidine;
2-phenyl-3-[(2-methoxy-5-trifluoromethylphenyl)methylamino]-4-(2-hydroxyethyl)pyrrolidine;
2-phenyl-3-[(2-methoxy-5-chlorophenyl)methylamino]-4(2-hydroxyethyl)pyrrolidine;
2-phenyl-3-[(2-methoxy-5-fluorophenyl)methylamino]-4(2-hydroxyethyl)pyrrolidine;
2-phenyl-3-[(2-methoxy-5-methoxyphenyl)methylamino]-4(2-hydroxyethyl)pyrrolidine;
2-phenyl-3-[(2-methoxy-5-phenoxyphenyl)methyl amino]-4(2-hydroxyethyl)pyrrolidine;
2-phenyl-3-[(2-methoxy-5-(N,N-dimethylamino)phenyl)methylamino]-4-(2-hydroxyethyl)pyrrolidine;
2-phenyl-3-[(2-methoxy-5-hydroxymethylphenyl)methylamino]-4-(2-hydroxyethyl)pyrrolidine;
2-phenyl-3-[(2-methoxy-5-nitrophenyl)methylamino]-4-(2-hydroxyethyl)pyrrolidine;
2-phenyl-3-[(2-methoxyphenyl)methylamino]-4-(2-hydroxyethyl)-5-hydroxymethylpyrrolidine;
2-phenyl-3-[(2-methoxyphenyl)methylamino]-4-(2-hydroxyethyl)-5-methoxymethylpyrrolidine; and
2-phenyl-3-[(2-methoxy-3-pyridyl)methylamino]-4-(2-hydroxyethyl)pyrrolidine;
(2SR, 3SR, 4RS)-2-diphenylmethyl-3-[(2-cyclopropylmethoxyphenyl)methylamino]-4-(2-hydroxyethyl)pyrrolidine;
(2SR, 3SR, 4RS)-2-diphenylmethyl-3-[(2-isopropoxyphenyl)methylamino]-4-(2-hydroxyethyl)pyrrolidine;
(2SR, 3SR, 4RS)-2-diphenylmethyl-3-[(2-isopropoxy-5-(1,1-dimethylethyl)phenyl)methylamino]-4-(2-hydroxyethyl)pyrrolidine;
(2SR, 3SR, 4RS)-2-diphenylmethyl-3-[(2-isopropoxy-5-(1-methylethyl)phenyl)methylamino]-4-(2-hydroxyethyl)pyrrolidine;
(1SR, 2SR, 3SR, 4RS)-1-aza-2-diphenylmethyl-3-[(2-cyclopropylmethoxyphenyl)methylamino]-bicyclo[2.2.1]heptane;
(1SR, 2SR, 3SR, 4RS)-1-aza-2-diphenylmethyl-3-[(2-methoxy-5-methoxyphenyl)methylamino]-bicyclo[2.2.1]heptane;
(1SR, 2SR, 3SR, 4RS)-1-aza-2-diphenylmethyl-3-[(2-methoxy-5-fluorophenyl)methylamino]-bicyclo[2.2.1]heptane;
(1SR, 2SR, 3SR, 4RS)-1-aza-2-diphenylmethyl-3-[(2-methoxy-5-phenylphenyl)methylamino]-bicyclo[2.2.1]heptane;
(1SR, 2SR, 3SR, 4RS)-1-aza-2-diphenylmethyl-3-[(2-trifluoromethoxyphenyl)methylamino]-bicyclo[2.2.1]heptane;
(1SR, 2SR, 3SR, 4RS)-3-aza-2-diphenylmethyl-3-[(2-isopropoxy-5-(1,1-dimethylethyl)phenyl)methylamino]bicyclo[2.2.1]heptane;
(1S, 2S, 3S, 4R)-1-aza-2-diphenylmethyl-3-[(2-methoxy-5-(N-methyl-N-acetamido)phenyl)methylamino]bicyclo[2.2.1]hepane;
(1S, 2S, 3S, 4R)-1-aza-2-diphenylmethyl-3-[(2-methoxy-5-(N-isopropyl-N-acetamido)phenyl)methylamino]bicyclo[2.2.1]heptane;
(1SR, 2SR, 3SR, 4RS)-1-aza-2-diphenylmethyl-3-[(2-isopropoxy-5-(1-methylethyl)phenyl)methylamino]bicyclo[2.2.1]heptane; and
(1SR, 2SR, 3SR, 4RS)-1-aza-2-diphenylmethyl-3-[(2-isopropoxyphenyl)methylamino]-bicyclo[2.2.1]heptane.

The present invention also relates to a pharmaceutical composition for treating or preventing a condition selected from the group consisting of inflammatory diseases (e.g., arthritis, psoriasis, asthma and inflammatory bowel disease), anxiety, depression or dysthymic disorders, colitis, psychosis, pain, gastroesophageal reflux disease, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising an amount of a compound of the formula I, or a pharmaceutically acceptable salt thereof, effective in treating or preventing such condition, and a pharmaceutically acceptable carrier.

The present invention also relates to a method of treating or preventing a condition selected from the group consisting of inflammatory diseases (e.g., arthritis, psoriasis, asthma and inflammatory bowel disease), anxiety, depression or dysthymic disorders, colitis, psychosis, pain, gastroesophageal reflux disease, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising administering to said mammal an amount of a compound of the formula I, or a pharmaceutically acceptable salt thereof, effective in treating or preventing such condition.

The present invention also relates to a pharmaceutical composition for antagonizing the effects of substance P in a mammal, including a human, comprising a substance P antagonizing amount of a compound of the formula I, or a pharmaceutically acceptable salt thereof, and a pharmaceutically acceptable carrier.

The present invention also relates to a method of antagonizing the effects of substance P in a mammal, including a human, comprising administering to said mammal a substance P antagonizing amount of a compound of the formula I, or a pharmaceutically acceptable salt thereof.

The present invention also relates to a pharmaceutical composition for treating or preventing a disorder in a mammal, including a human, resulting from an excess of substance P, comprising a substance P antagonizing amount of a compound of the formula I, or a pharmaceutically acceptable salt thereof, and a pharmaceutically acceptable carrier.

The present invention also relates to a method of treating or preventing a disorder in a mammal, including a human, resulting from an excess of substance P, comprising administering to said mammal a substance P antagonizing amount of a compound of the formula I, or a pharmaceutically acceptable salt thereof.

The present invention also relates to a pharmaceutical composition for treating or preventing a condition selected from the group consisting of .inflammatory diseases (e.g., arthritis, psoriasis, asthma and inflammatory bowel disease), anxiety, depression or dysthymic disorders, colitis, psychosis, pain, gastroesophageal reflux disease, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising an amount of a compound of the formula I, or a pharmaceutically acceptable salt thereof, effective in antagonizing the effect of substance P at its receptor site, and a pharmaceutically acceptable carrier.

The present invention also relates to a method of treating or preventing a condition selected from the group consisting of inflammatory diseases (e.g., arthritis, psoriasis, asthma and inflammatory bowel disease), anxiety, depression or dysthymic disorders, colitis, psychosis, pain, gastroesophageal reflux disease, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising administering to said mammal an amount of a compound of the formula I, or a pharmaceutically acceptable salt thereof, effective in antagonizing the effect of substance P at its receptor site.

The present invention also relates to a pharmaceutical composition for treating or preventing a disorder in a mammal, including a human, the treatment or prevention of which is effected or facilitated by a decrease in substance P mediated neurotransmission, comprising an amount of a compound of the formula I, or a pharmaceutically acceptable salt thereof, .effective in antagonizing the effect of substance P at its receptor site, and a pharmaceutically acceptable carrier.

The present invention also relates to a method of treating or preventing a disorder in mammal, including a human, the treatment or prevention of which is effected or facilitated by a decrease in substance P mediated neurotransmission, comprising administering to said mammal an amount of a compound of the formula I, or a pharmaceutically acceptable salt thereof, effective in antagonizing the effect of substance P at its receptor site.

The present invention also relates to a pharmaceutical composition for treating or preventing a disorder in a mammal, including a human, the treatment or prevention of which is effected or facilitated by a decrease in substance P mediated neurotransmission, comprising an amount of a compound of the formula I, or a pharmaceutically acceptable salt thereof, effective in treating or preventing such disorder, and a pharmaceutically acceptable carrier.

The present invention also relates to a method of treating or preventing a disorder in mammal, including a human, the treatment or prevention of which is effected or facilitated by a decrease in substance P mediated neurotransmission, comprising administering to said mammal an amount of a compound of the formula I, or a pharmaceutically acceptable salt thereof, effective in treating or preventing such disorder.

The compounds of the formulae I through VII have chiral centers and therefore exist in different enantiomeric forms. This invention relates to all optical isomers and all stereoisomers of compounds of the formulae I through VII, and mixtures thereof.

Formulae I through VII above include compounds identical to those depicted but for the fact that one or more hydrogen or carbon atoms are replaced by radioactive isotopes thereof. Such radiolabelled compounds are useful as research and diagnostic tools in metabolism pharmokinetic studies and in binding assays. Specific applications in research include radioligand binding assays, autoradiography studies and in vivo binding studies, while specific applications in the diagnostic area include studies of the substance P receptor in the human brain in in vivo binding in the relevant tissues for inflammation, e.g. immune-type cells or cells that are directly involved in inflammatory bowel disorders and the like. Included among the radiolabelled forms of compounds of the formulae I through VII are the tritium, $C^{11}$ and $C^{14}$ isotopes thereof.

DETAILED DESCRIPTION OF THE INVENTION

Schemes 1-4 below illustrate methods of preparing compounds of the formulae I through VII. In the reaction schemes and discussion that follow, unless otherwise indicated, $R^1$ through $R^{24}$ are defined as above.

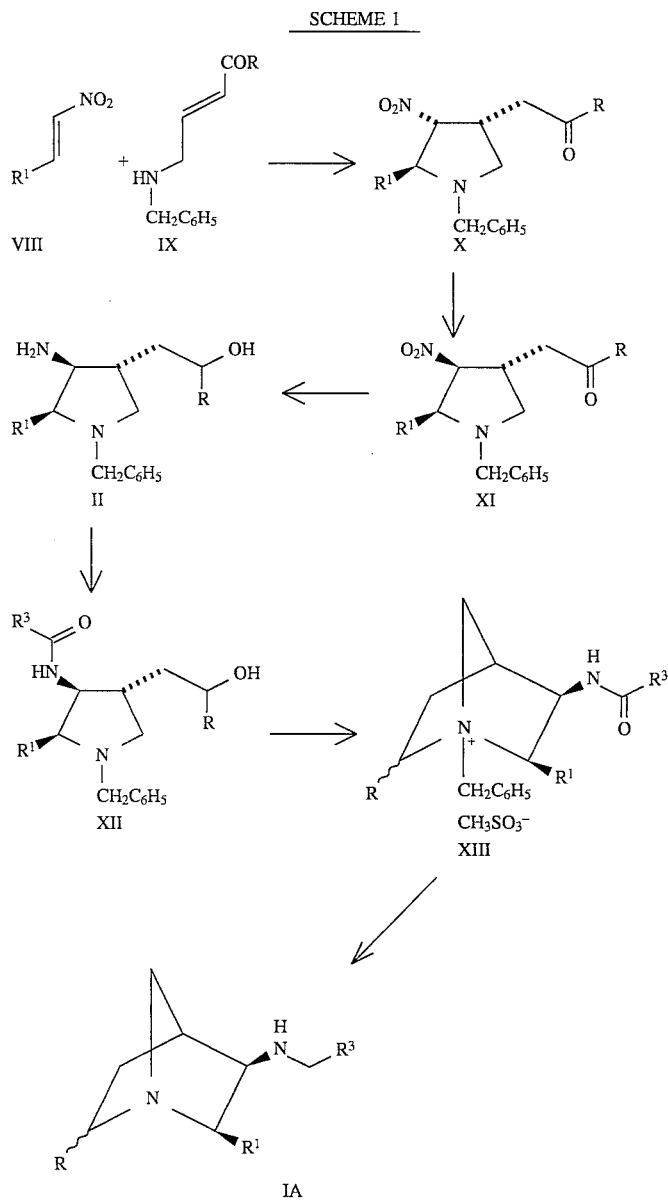

SCHEME 2
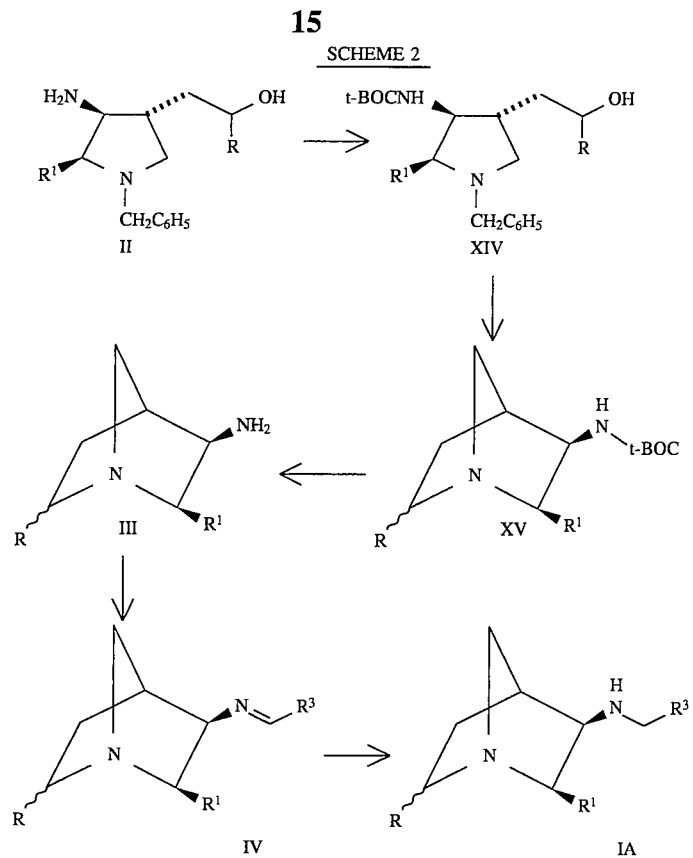
SCHEME 3
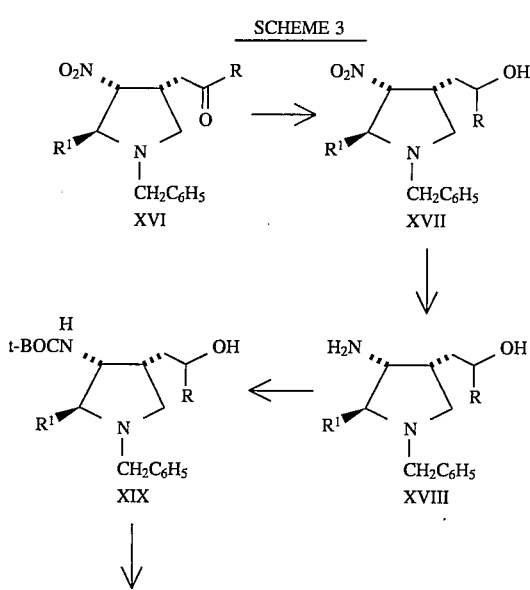
-continued
SCHEME 3
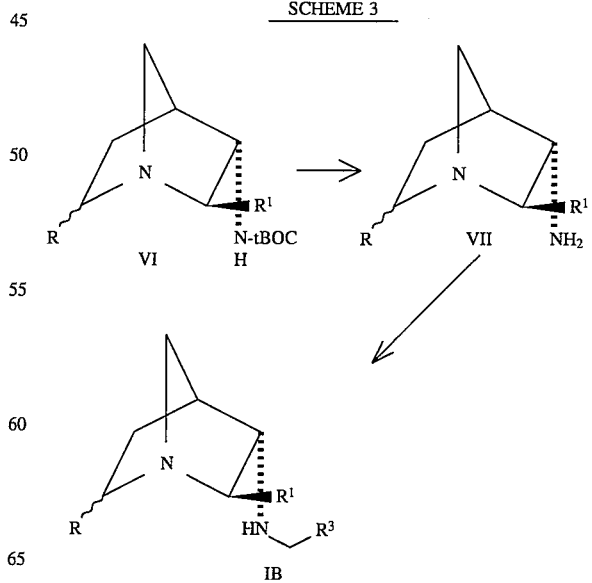

SCHEME 4

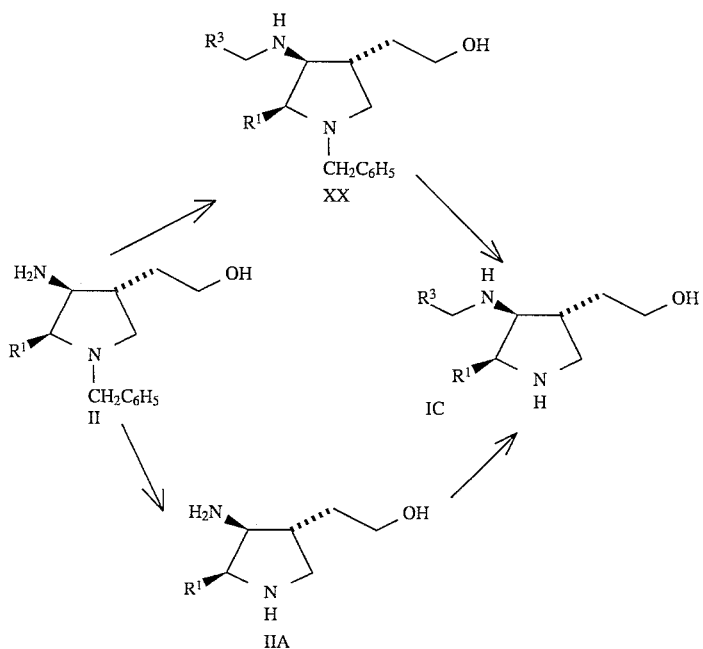

Referring to scheme 1, a compound of the formula VIII is reacted with a compound of the formula IX, wherein R is selected from hydrogen, ($C_1$–$C_4$)alkyl, phenyl, benzyl, O-($C_1$–$C_4$) alkyl, O-phenyl and O-benzyl, to produce a compound of the formula X. (Hereinafter in this document, except where otherwise noted, R will be defined as above.) This reaction is typically carried out in an inert solvent such as a lower alcohol, benzene, toluene, acetonitrile or tetrahydrofuran (THF) at a temperature from about 0° C. to about 60° C. It is preferably carried out in ethanol or methanol at about room temperature.

The compound of formula X so formed is then converted into a compound which is identical to it but for the fact that $R^1$ and the nitro group are cis to each other (i.e., a compound of the formula XI) by the following procedure. First, the compound of formula X is reacted with a base such as lithium diisopropylamide (LDA), 1,8-diazabicyclo[5.4.0] undec-7-ene (DBU), DBU in combination with lithium chloride, 1,5,7-triazabicyclo[4.4.0]dec-5-ene or potassium t-butoxide. Typically, this reaction is conducted at a temperature of about room temperature to about 80° C., preferably about 60° C. The preferred base is potassium t-butoxide when $R^1$ is diphenylmethyl and DBU when $R^1$ is phenyl. Suitable solvents for this reaction include mixtures of a lower alcohol and another inert solvent such as THF or ether in a 1:3 ratio. Preferably, the solvent is a 1:3 mixture of methanol and THF. However, when $R^1$ is phenyl, the preferred solvent is ether alone.

Quenching the reaction mixture from the above step with acetic acid of trimethylacetic acid yields the desired compound of formula XI. When $R^1$ is phenyl, however, and the reaction is carried out in ether using DBU as a base, then, no quench is necessary. In that case, the compound of formula XI crystallizes directly from the reaction mixture.

Reduction of the nitro group of the compound of formula XI followed by the reduction of the —COR group produces the corresponding compound of formula II. The nitro group may be reduced using one of several reducing agents, including Raney nickel/hydrogen, 10% palladium on charcoal/hydrogen, and aluminum amalgam. Preferably, this reduction is carried out using Raney nickel in ethanol under a hydrogen gas pressure of about three atm at a temperature of about 28° C. Temperatures from about 10° C. to about 60° C. and pressures from about 1 to about 10 atmospheres are also suitable.

Reduction of the —COR group is generally accomplished using lithium aluminum hydride, diisobutylaluminum hydride, Vitride®, borane-THF or sodium or lithium borohydride in an inert solvent such as ether, toluene, THF or dimethoxyethane. It is preferably accomplished using lithium aluminum hydride in THF. When sodium borohydride is used, the reaction is preferably carried out in methanol, ethanol or a mixture of methanol and THF. The reaction temperature may range from about –20° C. to about 15° C., with about 0° C. being preferred.

If R is either O-($C_1$–$C_4$)alkyl, O-phenyl or O-benzyl in the compound of formula XI, the above reduction will yield a compound of the formula II wherein R is hydrogen and the subsequent steps in Scheme 1 will yield compounds of the formula XII, XIII and IA wherein R is hydrogen. If R is either hydrogen, alkyl, phenyl or benzyl in the compound of formula XI, the above reduction will yield a compound of the formula II wherein R is defined as in the compound of formula XI and the subsequent steps in scheme 1 will yield compounds of the formula XII, XIII and IA wherein R is defined as in the compound of formula XI.

The compound of formula II formed in the above step is then reacted with a compound of the formula $$\overset{O}{\underset{\|}{R^3CCl}}$$

in the presence of a base to form a compound having the formula XII. This reaction is usually conducted in an inert solvent such as methylene chloride or pyridine, preferably methylene chloride, at a temperature from about –20° C. to about 20° C., preferably about 0° C. Examples of bases that may be used are secondary and tertiary amines such as pyridine and triethylamine. Pyridine is preferred.

Activation of the alcohol of formula XII followed by heating to achieve closure of the second pyrrolidine ring (and thus formation of a bicyclic ring) produces the corresponding compound of formula XIII. The acylation step is generally carried out by reaction with an acylating agent such as mesyl chloride, tosyl chloride or trifluoromethanesulfonyl anhydride in the presence of a base. Suitable inert solvents for this step include methylene chloride, benzene and toluene. Suitable temperatures range from about −20° C. to about 25° C. About 0° C. is preferred. Examples of bases that may be used are secondary and tertiary amines such as pyridine, triethylamine (TEA), N-methylmorpholine and diisopropylethylamine. Preferably, the acylation is carried out using mesyl chloride in the presence of pyridine at about 0° C.

Heating the product of the above reaction in a lower alcohol such as methanol, ethanol or isopropanol results in cyclization of the second pyrrolidine ring with formation of the bicyclic ring. Cyclization will occur at temperatures from about 50° C. to about 110° C. It is preferably conducted at about 65° C.

The compound of formula XIII so formed may be converted to the corresponding compound of the formula IA by the following procedure. First, the compound of formula XIII is reacted with hydrogen gas and palladium on charcoal (e.g., 10% palladium on charcoal). Typically, a polar inert solvent such as a lower alcohol or ethyl acetate is used, and the reaction is run at a temperature from about 15° C. to about 45° C. for about 0.5 hours to about 24 hours. The reaction is preferably conducted in methanol at room temperature for about 10 hours. The product of this reaction is then reacted with borane-THF, borane-dimethylsulfide dimethylsulfide or diisobutyl aluminum hydride, preferably with borane-THF, to form the desired product having the formula IA. Suitable solvents for this reaction include ether, dimethoxyethane and THF. THF is preferred. This reaction is usually run at a temperature from about 40° C. to about 100° C., with 65° C. being preferred.

An alternative procedure for preparing compounds of the formula I wherein R9, together with the carbon to which it is attached, the nitrogen of pyrrolidine ring depicted in structure I, the carbon to which $R^8$ is attached and the carbon to which $R^5$ and $R^6$ are attached, form a second pyrrolidine ring (and thus a bicyclic ring) is described in Example 2.

Another alternate procedure for preparing compounds of the formula I that contain two pyrrolidine rings and are thus bicyclic in nature is illustrated in scheme 2. Referring to scheme 2, a compound of the formula II, wherein R is hydrogen, $(C_1-C_4)$alkyl, phenyl or benzyl, is reacted with a nitrogen protecting group such as di-t-butyldicarbonate ((t-BOC)$_2$O) or carbobenzyloxycarbonyl chloride (CBz-Cl) in the presence of a base such as sodium or potassium carbonate, sodium or potassium bicarbonate, triethylamine (TEA), DBU or N-methylmorpholine, or without a base in the presence of bistrimethylsilylacetamide, in an inert solvent such as ether, methylene chloride, dichloroethane, chloroform, benzene or THF or a two phase mixture of chloroform-water, methylene chloride-water or dichloroethane-water. Temperatures may range from about room temperature to about 100° C. This reaction is preferably conducted using t-BOC dicarbonate in methylene chloride in the presence of an aqueous base at the reflux temperature of the mixture.

The above reaction produces a compound of the formula XIV, which may be converted to the corresponding compound of the formula XV as follows. The compound of formula XIV is reacted with mesyl chloride or tosyl chloride in the presence of a base followed by heating in an appropriate solvent, using the procedure described above for preparing compounds of the formula XIII from compounds of the formula XII. This reaction produces, as an intermediate, a quaternary ammonium mesylate salt identical to compound XIII (depicted in scheme 1), except that the

substituent is replaced by -t-BOC. The intermediate is then reduced (e.g., using hydrogen and palladium on charcoal) in the manner described above for the first step in the conversion of compounds of the formula XIII to compounds of the formula IA.

Reaction of the compound of formula XV formed in the preceding step with a strong acid yields a salt containing the corresponding compound of formula III and the chosen acid in a 1:2 ratio. Appropriate acids for this reaction include hydrogen chloride (gas), hydrochloric acid, sulfuric acid, hydrobromic acid, hydrogen bromide (gas) and trifluoroacetic acid. Hydrogen chloride (gas) is preferred. Suitable solvents include THF, benzene, toluene, ether, methylene chloride and ethyl acetate, with ethyl acetate being preferred. The reaction may be carried out at temperatures from about 0° C. to about 100° C. and is preferably carried at about 77° C.

Neutralization of the acid salt with a base followed by reaction with a compound of the formula

produces the corresponding compound of formula IV. The neutralization is usually accomplished using an aqueous base (e.g., a metal hydroxide, carbonate or bicarbonate), TEA or DBU, preferably sodium or potassium hydroxide, at a temperature from about 0° C. to about 40° C., preferably about room temperature. The reaction with the compound of formula

is generally carried out in an inert solvent such as benzene, toluene or another solvent that separates water, or in an inert solvent such a THF or methylene chloride in the presence of a drying agent (e.g., using a Dean Stark® trap or molecular sieves). Suitable temperatures for this reaction range from about 80° C. to about 111° C. The reflux temperature of the solvent is preferred.

The resulting compound of formula IV may be converted to the corresponding compound of the formula IA by reacting it with a reducing agent. Suitable reducing agents include sodium borohydride, hydrogen and a metal catalyst, sodium triacetoxyborohydride, sodium cyanoborohydride, zinc and hydrochloric acid and formic acid. Sodium triacetoxyborohydride is preferred. This reduction is usually conducted in an inert solvent such as dichloroethane (DCE), dichloromethane (ECM), THF, methylene chloride, a lower alcohol, chloroform or acetic acid, preferably DCE, at a temperature from about −20° C. to about 60° C., preferably about room temperature.

In the compounds of formulae XIV, XV, III, IV and IA prepared by the method described above and illustrated in scheme 3, R will be the same as in the compound of formula II from which they were made.

Scheme 3 illustrates a method of preparing compounds of the formula I that are bicyclic (i.e., that contain two pyrrolidine rings) and wherein $R^1$ and the benzylamino group are trans to each other as depicted in structure IB.

Referring to scheme 3, a compound of the formula XVI is reduced by reaction with borane-THF complex, with or without sodium borohydride, in an inert solvent such as THF, DME or diethylether to yield the corresponding hydroxy compound of formula XVII. In the compound of formula XVII so formed, R will be hydrogen if R was either $O-(C_1-C_4)$alkyl, O-phenyl or O-benzyl in the compound of formula XVI from which it was made. (If R was either hydrogen, $(C_1-C_4)$alkyl, phenyl or benzyl in the compound of formula XVI, R will have the same value in both the compound of formula XVII and all subsequent compounds; depicted in scheme 3). The reaction temperature can range from about 0° C. to about 100° C. It is preferably about 0° C. initially and about the reflux temperature of the solvent subsequently.

Reduction of the nitro group of the compound of formula XVII yields the corresponding compound of formula XVIII. Suitable reducing agents include Raney nickel/hydrogen, 10% palladium on charcoal/hydrogen, and aluminum amalgam. Preferably, the reduction is carried out using Raney nickel in ethanol under a hydrogen gas pressure of about 3 atm and at a temperature of about 25° C. Temperatures from about 10° C. to about 60° C. and pressures from about 1 to about 10 atmospheres are also suitable.

The compound of formula XVIII formed in the above step may be converted into the desired compound of the formula IB by the procedure illustrated in scheme 2 and described above for conversion of compounds of the formula II into compounds of the formula IA. Alternatively, compounds of the formula VII, as shown in scheme 3, may be converted into compounds of the formula IB by a one step procedure rather than the two step procedure (III→IV→IA) shown in scheme 2 which involves separation of the imine of formula IV. This procedure, which is exemplified in Example 9F, involves combining procedures III→IV and IV→IA illustrated in scheme 2 and described above.

Scheme 4 illustrates two methods of preparing compounds of the formula IC containing only one pyrrolidine ring (i.e., those compounds wherein $R^9$ does not form part of a 5 membered ring). These methods are represented by reaction sequences II→XX→IC and II→IIA→IC in scheme 4 and exemplified in, respectively, Examples 10 and 11.

According to the first method (II→XX→IC), a compound of the formula II is subjected to reductive amination, either as described in steps III→IV→IA of scheme 2 or as described in steps VII→IB of scheme 3, to produce a compound of the formula XX. The compound is then reduced as described above for the first step of the conversion of compounds of the formula XIII into compounds of the formula IA in scheme 1.

According to the second method (II→IIA→IC), a compound of the formula II is reduced as described above for step XIII→IA of scheme 1 to form the corresponding compound of formula IIA which is then subjected to reductive amination as described above for step II→XX of scheme 4.

The preparation of other compounds of the formula I not specifically described in the foregoing experimental section can be accomplished using combinations of the reactions described above that will be apparent to those skilled in the art.

In each of the reactions discussed or illustrated in schemes 1 to 4 above, pressure is not critical unless otherwise indicated. Pressures from about 0.5 atmospheres to about 5 atmospheres are generally acceptable, and ambient pressure, i.e. about 1 atmosphere, is preferred as a matter of convenience. The starting materials used to prepare the final product substance P receptor antagonist compounds of this invention are either well-known in the prior art, or else they are easily prepared by those skilled in the art from readily available materials in accordance with standard organic procedures previously described in the chemical literature. For instance, methyl 4-bromocrotonate (an ultimate starting material that readily leads to a starting compound of structural formula IX, as described in Example 1A) is a commercially available material that is readily provided by the Aldrich Chemical Company, Inc., of Milwaukee, Wis., as early as 1984, according to their Supplement to the 1984–1985 Catalog/Handbook of Fine Chemicals. In like manner, the nitrostyrene starting material of Example 2A (which is a structural formula VIII type compound), as well as many of the mono-substituted aromatic acylhalide and aldehyde reagents employed as reactants in the later Examples of the instant specification also find their source in commerce from this same chemical entity. On the other hand, some of the polysubstituted aromatic aldehyde reagents employed as starting materials in this connection are best prepared by using known chemical literature procedures taken from the established prior art, as hereinafter cited at the appropriate points in the test of the actual working Examples.

The novel compounds of the formula I and the pharmaceutically acceptable salts thereof are useful as substance P antagonists, i.e., they possess the ability to antagonize the effects of substance P at its receptor site in mammals, and therefore they are able to function as therapeutic agents in the treatment of the aforementioned disorders and diseases in an afflicted mammal.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the Formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

The compounds of Formula I and their pharmaceutically acceptable salts exhibit substance P receptor-binding activity and therefore are of value in the treatment and prevention of a wide variety of clinical conditions the treatment or prevention of which are effected or facilitated by a decrease in substance P mediated neurotransmission. Such conditions include inflammatory diseases (e.g., arthritis, psoriasis, asthma and inflammatory bowel disease), anxiety, depression or dysthymic disorders, colitis, psychosis, pain, gastroesophageal reflux disease, allergies such as eczema and rhinitis, chronic obstructive airways disease, hypersensitivity disorders such as poison ivy, vasospastic diseases such as angina, migraine and Reynaud's disease, fibrosing and collagen diseases such as scleroderma and eosinophilic fascioliasis, reflex sympathetic dystrophy- such as shoulder/hand syndrome, addiction disorders such as alcoholism, stress related somatic disordered, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis. Hence, these compounds are readily adapted to therapeutic use as substance P antagonists for the control and/or treatment of any of the aforesaid clinical conditions in mammals, including humans.

The compounds of the formula I and the pharmaceutically acceptable salts thereof can be administered via either the oral, parenteral or topical routes. In general, these compounds are most desirably administered in dosages ranging from about 1.0 mg up to about 1500 mg per day, preferably from about 1 to about 100 mg per day, although variations will necessarily occur depending upon the weight and condition of the subject being treated and the particular route of administration chosen. However, a dosage level that is in the range of about 0.07 mg to about 21 mg per kg of body weight per day is most desirably employed. Variations may nevertheless occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The compounds of the invention may be administered alone or in combination with pharmaceutically acceptable carriers or diluents by either of the three routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The activity of the compounds of the present invention as substance P antagonists is determined by their ability to inhibit the binding of substance P at its receptor sites in bovine caudate tissue, employing radioactive ligands to visualize the tachykinin receptors by means of autoradiography. The substance P antagonizing activity of the herein described compounds may be evaluated by using the standard assay procedure described by M. A. Cascieri et al., as reported in the *Journal of Biological Chemistry*, Vol. 258, p. 5158 (1983). This method essentially involves determining the concentration of the individual compound required to reduce by 50% the amount of radiolabelled substance P ligands at their receptor sites in said isolated cow tissues, thereby affording characteristic $IC_{50}$ values for each compound tested.

In this procedure, bovine caudate tissue is removed from a $-70°$ C. freezer and homogenized in 50 volumes (w./v.) of an ice-cold 50 mM Tris (i.e., trimethamine which is 2-amino-2-hydroxymethyl-1,3-propanediol) hydrochloride buffer having a pH of 7.7. The homogenate is centrifuged at 30,000× G for a period of 20 minutes. The pellet is resuspended in 50 volumes of Tris buffer, rehomogenized and then recentrifuged at 30,000× G for another twenty minute period. The pellet is then resuspended in 40 volumes of ice-cold 50 mM Tris buffer (pH 7.7)containing 2 mM of calcium chloride, 2 mM of magnesium chloride, 40 g/ml of bacitracin, 4µg/ml of leupeptin, 2µg of chymostatin and 200 g/ml of bovine serum albumin. This step completes the production of the tissue preparation.

The radioligand binding procedure is then carried out in the following manner, viz., by initiating the reaction via the addition of 100 µl of the test compound made up to a concentration of 1 µM, followed by the addition of 100 µl of radioactive ligand made up to a final concentration 0.5 mM and then finally by the addition of 800 µl of the tissue preparation produced as described above. The final volume is thus 1.0 ml, and the reaction mixture is next vortexed and incubated at room temperature (ca. 20° C.) for a period of 20 minutes. The tubes are then filtered using a cell harvester, and the glass fiber filters (Whatman GF/B) are washed four times with 50 mM of Tris buffer (pH 7.7), with the filters having previously been presoaked for a period of two hours prior to the filtering procedure. Radioactivity is then determined in a Beta counter at 53% counting efficiency, and the $IC_{50}$ values are calculated by using standard statistical methods.

The anti-psychotic activity of the compounds of the present invention as neuroleptic agents for the control of various psychotic disorders is determined primarily by a study of their ability to suppress substance P-induced or substance P agonist induced hypermotility in guinea pigs. This study is carried out by first dosing the guinea pigs with a control compound or with an appropriate test compound of the present invention, then injecting the guinea pigs with substance P or a substance P agonist by intracerebral administration via canula and thereafter measuring their individual locomotor response to said stimulus.

The present invention is illustrated by the following examples. It will be understood, however, that the invention is not limited to the specific details of these examples.

EXAMPLE 1

(1SR, 2SR, 3SR,4RS)-1-aza-2-Diphenylmethyl-3-(2-methoxyphenyl)methylaminobicyclo[2.2.1]heptane A. Methyl-4-phenylmethylamino-2-butene-1-carboxylate A suspension of 100 g 50% potassium fluoride/Celite® in 1400 ml of acetonitrile was treated with 29.93 g (279.5 mmol) benzylamine and 11.30 g (558 mmol) triethylamine (all the aforementioned reagents, solvents and starting materials are readily commercially available from the Aldrich Chemical Company, Inc., of Milwaukee, Wis.; see Supplement to the 1984–1985 Aldrich Catalog/Handbook of Fine Chemicals) and the mixture was cooled to 0°–5° C. The suspension was treated with 50 g (279.5 mmol) of methyl-4-bromocrotonate (Aldrich) for over 25 min. The ice bath was then removed. After the reaction mixture was stirred for approximately one hour and was judged complete by thin layer analysis (elution with 94-5-1; $CH_2Cl_2$-$CH_3OH$-$NH_4OH$), the suspension was filtered and the filtrate was evaporated. The residue was partitioned between 1 L saturated aqueous bicarbonate and washed with 500 mL of ether (3X). The combined organics were washed once with aqueous bicarbonate and then saturated brine. The solution was dried and evaporated in vacuo to provide an oil (32.64 g 53.4%) which was used directly without purification.

$^1$H NMR (CDCl$_3$, 250 MHz) δ7.38–7.24 (m, 5H) , 7.09–6.98 (dt, 1H, J=15.7 Hz, J=5.4 Hz), 6.08–6.01 (dt, 1H, J-15.7 Hz, J=1.8 Hz), 3.82 (2H, s), 3.75 (3H, s), 3.45–3.42 (dd, 2H, J=5.4 Hz, J=1.8 Hz), 1.45 (br s, 1H) ppm;

$^{13}$C NMR (CDCl$_3$, 75 MHz) δ166.8, 147.0, 139.8, 128.5, 128.1, 127.1, 121.2, 53.3, 51.5, 49.5 ppm.

IR (CHCl$_3$) λ1720, 1660 cm$^{-1}$. Mass spectrum m/e 204 (p-15).

B. 3,3-diphenyl-1-nitroprop-1-ene

Fifty grams (254.78 mmol) of diphenylacetaldehyde (Aldrich) and 18.66 g (305.73 mmol) of nitromethane was dissolved in 635 mL of dichloromethane. The stirred solution was treated with 35 g of 3Å molecular sieves followed by 11.64 g (76.43 mmol) 1,8-diazabicyclo[5.4.0]undec-7-ene (DBU) (Aldrich) and stirred overnight at room temperature. The reaction mixture was filtered and the filtrate was treated with 700 mL of 2N aqueous HCl. The organic layer was separated and washed with saturated brine solution, dried with sodium sulfate and evaporated in vacuo. The residue was treated with 600 mL of hexane and stirred overnight whereupon crystallization occurred. After isolation there was obtained 38.22 g (58%) of 3,3-diphenyl-2-hydroxy-l-nitropropane as a pale yellow solid which was used directly in the following step.

A solution of 32.81 g (127.5 mmol) of the adduct prepared above in 650 mL of dichloromethane was cooled to 0° C. and was treated with 17.53 g (153 mmol) of methanesulfonyl chloride. The resultant solution was treated immediately and without hesitation with a second solution of 25.81 mL (255 mmol) of triethylamine in 250 mL methylene chloride over a period of 25 min. The reaction was stirred for 1 hour and then quenched into ether and a saturated brine solution. The organic layer was dried and evaporated in vacuo. There was obtained 33 g of a dark oil which was used without purification.

$^1$H NMR (CDCl$_3$, 250 MHz) δ7.78–7.70 (dd, 1H, J=13.2 Hz, J=7.2 Hz), 7.39 –7.16 (m, 10 H), 6.83–6.77 (dd, 1H, J=13.2 Hz, J-3.5 Hz), 5.0–4.95 (d, 1H, J=7.2 Hz) ppm.

$^{13}$C NMR (CDCl$_3$, 62.9 MHz) 143.8, 141.2, 139.8, 129.0, 128.4, 127.6, 50.1 ppm.

C. (2SR, 3RS, 4RS)-1N-phenylmethyl-2-diphenylmethyl-3-nitro-4-carbomethoxymethyl-pyrrolidine A solution of the above prepared nitroolefin (5.11 g, 21.36 mmol) and 5.11 g (24.9 mmol) of previously prepared methyl-4-phenylmethylamino-2-butene-1-carboxylate (the product of Example 1A) in 400 mL methanol was stirred at room temperature for 16 hours. Almost immediate precipitation was evident and by the end of the reaction time a thick slurry was formed. The reaction mixture was filtered directly to afford 4.94 g (52%) of the desired product.

$^1$H NMR (CDCl$_3$, 250 MHz) δ7.42–7.04 (m, 15H), 4.89–4.86 (d, 1H, J=6.7 Hz), 4.31–4.28 (d, 1H, J=9.1 Hz), 4.04–4.01 (d, 1H, J=9.2 Hz), 3.61 (s, 3H), 3.47 (br.s, 2H), 3.05–2.99 (dd, 1H, J=8.8 Hz, J=6.3 Hz), 2.80–2.73 (m, 1H), 2.50–2.41 (dd, 1H, J=11.7 Hz, J=8.9 Hz), 2.25–2.22 (d, 2H, J=7.3 Hz) ppm.

$^{13}$C NMR (CDCl$_3$, 75.5 MHz) δ171.3, 141.5, 141.1, 139.1, 129.0, 128.9, 128.7, 128.6, 128.3, 128.1, 127.1, 127.0, 92.7, 72.1, 60.7, 57.2, 56.7, 51.9, 38.2, 31.8 ppm. Mass spectrum m/e (FAB) 445 (p+l), 277, 231.

IR (CHCl$_3$) λ1735, 1545, 1359 cm$^{-1}$.

D. 2SR, 3SR, 4RS)-1N-phenylmethyl-2-diphenylmethyl-3-nitro-4-carbomethoxymethylpyrrolidine A solution of 264 mg (0.59 mmol) of the previously prepared pyrrolidine (the product of Example 1D) in 150 mL of THF and 50 mL of methanol was treated with 1.63 mL (1.63 mmol) of 1M potassium t-butoxide in THF. The reaction mixture was heated to reflux for 30 min. The solution was cooled to room temperature and quenched with a 7 mL methanol solution containing 288 mg (2.82 mmol) trimethylacetic acid. The solution was stirred for 5 min and was then diluted with 125 mL of saturated aqueous bicarbonate: solution and 400 mL of water to dissolve the precipitate that formed. The aqueous mixture was extracted with methylene chloride (5×70 mL) and the combined organic phase was washed with 200 mL of saturated brine solution. The organic solution was dried with sodium sulfate and evaporated in vacuo. The residue was chromatographed on silica gel eluting with 10% ethyl acetate in hexane. The fractions containing the more polar material were combined and evaporated to afford 195 mg (75%) of the desired 3SR-nitropyrrolidine.

$^1$H NMR (CDCl$_3$, 300 MHz) δ7.48–6.98 (m, 15H), 4.87–4.83 (t, 1H, J=6.9 Hz), 4.37–4.34 (d, 1H, J=10.2 Hz), 4.23–4.16 (dd, 1H, J=10.1 Hz, J=7.2 Hz), 3.61 (s, 3H), 3.48–3.44 (d, 1H, J=12.9 Hz), 3.25–3.07 (m, 3H), 2.53–2.37 (m, 2H), 2.21–2.14 (t, 1H, J=9.8 Hz) ppm.

$^{13}$C NMR (CDCl$_3$, 75.5 MHz) δ171.2, 142.0, 141.3, 139.1, 128.8, 128.6, 128.5, 128.5, 128.2, 127.9, 127.1, 127.0, 126.9, 92.6, 68.9, 58.3, 57.1, 52.2, 51.8, 40.3, 35.7, 31.9 ppm. Mass spectrum m/e (FAB) 445 (p+1).

E. (2SR, 3SR, 4RS)-1N-phenylmethyl-2-diphenylmethyl-3-amino-4-carbomethoxymethypyrrolidine A solution of 164 mg (0.37 mmol) of the compound prepared above was dissolved in 4 mL of THF and 50 mL of methanol and was treated with 650 mg of water washed RaNi (pH 7) stored under ethanol. The mixture was placed in a Parr pressure bottle and placed under 50 psi hydrogen for a period of approximately 4.5 hours. The reaction mixture was purged with nitrogen and then filtered. The filtrate was evaporated in vacuo and the residue (150 mg) was used directly in the next step.

$^1$H NMR (CDCl$_3$, 250 MHz) δ7.53–7.04 (m, 15H), 4.24–4.21 (d, 1H, J=9.1 Hz), 3.63–3.57 (m, obs, 1H), 3.61 (s, 3H), 3.33–3.28 (d, 1H, J=12.6 Hz), 3.14–3.07 (dt, 2H, J=6.7 Hz), 2.85–2.80 (d, 1H, J=12.7 Hz), 2.85–2.47 (dd, 1H, J=15.3 Hz, J=6.0 Hz), 2.30–2.12 (m, 2H), 1.91–1.84 (dd, 1H, J=9.6 Hz, J=8.8 Hz) ppm.

$^{13}$C NMR (CDCl$_3$, 62.9 MHz) δ173.0, 143.8, 143.5, 139.5, 128.9, 128.7, 128.6, 128.5, 128.1, 128.0, 127.9, 126.7, 126.5, 126.3, 70.1, 61.0, 59.8, 58.1, 53.4, 51.6, 41.6, 37.2 ppm. Mass spectrum. m/e (FAB) 415 (p+1), 247, 167.

IR (CHCl$_3$) λ3,578, 1732, 1185 cm$^{-1}$.

F. (2SR, 3SR, 4RS)-1N-phenylmethyl-2-diphenylmethyl-3-amino-4-(2-hydroxyethyl)pyrrolidine A solution of lithium aluminum hydride was prepared by dilution of 0.72 mL of 1M reagent in THF with 11 mL of anhydrous THF. The solution was cooled to 0° C. and was treated with 150 mg of the material from the previous step (the product of Example 1E) in 5 mL THF. The reaction mixture was stirred for 20 min at 0° C. The reaction was quenched by the sequential addition of 28 μL water, 28 μL 15% aqueous sodium hydroxide and 86 μL water. The resultant precipitate was granulated for 15 min and the slurry was filtered through Celite®. The residue after evaporation was chromatographed on silica gel eluting with CH$_2$Cl$_2$, CH$_3$OH, NH$_4$OH (97:2:1) to afford 93 mg of the desired product (67%).

$^1$H NMR (CDCl$_3$, 250 MHz) δ7.53–6.99 (m, 15 H), 4.13–4.10 (d, 1H, J=9.0 Hz), 3.68–3.59 (m, 2H), 3.52–3.42 (dt, 1H, J=11.4 Hz), 3.28–3.21 (t, 1H, J=9.0 Hz), 3.15–3.11 (d, 1H, J=12.4 Hz), 2.89–2.84 (dd, 1H, J=9.0 Hz, J=5.9 Hz), 2.82–2.77 (d, 1H, J=12.3 Hz), 1.93–1.86 (dd, 1H, J=11.0 Hz, J=9.2 Hz), 1.82–1.39 (m, 3H) ppm.

$^{13}$C NMR (CDCl$_3$, 62.9 MHz) δ143.6, 142.9, 139.4, 129.6, 129.0, 128.7, 128.4, 127.9, 126.6, 126.5, 70.5, 62.1, 61.7, 60.2, 58.8, 54.3, 46.1, 35.9 ppm.

IR (CHCl$_3$) λ3001, 1601, 1189 cm$^{-1}$.

G. (2SR, 3SR, 4RS)-1N-phenylmethyl-2-diphenylmethyl-3-(2-methoxybenzamido)-4-(2-hydroxyethyl)pyrrolidine A solution of 65 mg (0.168 mmol) of the product from above (the product of Example 1F) in 6 mL methylene chloride was cooled to 0° C. The solution was treated with 13.3 mg (0.168 mmol) pyridine followed by the slow dropwise addition of 28.7 mg (0.168 mmol) o-anisoyl chloride (Aldrich). Thin layer analysis indicated the formation of two products which were less polar compared with the starting amine (elution with CH$_2$Cl$_2$, CH$_3$OH, NH$_4$OH, 94:5:1). The reaction mixture was quenched by the addition of 10 mL of water. The organic layer was separated and the organics were washed sequentially with water and saturated brine solution and then dried and evaporated. The residue was chromatographed on silica gel with CH$_2$Cl$_2$, CH$_3$OH, NH$_4$OH, 98:1:1 to afford 71 mg of the more polar of the two compounds as the desired product (74% yield).

$^1$H NMR (CDCl$_3$, 250 MHz) δ8.40–8.36 (d, 1H, J=8.4 Hz), 8.10–8.06 (dd, 1H, J=7.8 Hz, J=1.8 Hz), 7.56–7.44 (m, 3H), 7.31–6.97 (m, 14H), 4.35–4.28 (m, 1H), 4.09–4.04 (d, obs, 1H), 4.04 (s, 3H), 3.86–3.81 (dd, 1H, J=8.4 Hz, J=5.9 Hz), 3.74–3.57 (m, 2H), 3.57–3.52 (d, 1H, J=12.9 Hz), 3.49–3.47 (m, 1H), 3.23–3.17 (dd, 1H, J=9.3 Hz, J=7.7 Hz), 2.90–2.85 (d, 1H, J=12.9 Hz), 2.08–2.04 (m, 1H), 1.96–1.89 (dd, 1H, J=9.3 Hz, J=8.0 Hz), 1.78–1.50 (m, 3H) ppm.

$^{13}$C NMR (CDCl$_3$, 62.9 MHz) δ164.9, 157.4, 143.3, 143.0, 139.9, 132.7, 132.2, 128.5, 128.3, 128.2, 128.1, 127.7, 126.7, 126.5, 126.2, 121.3, 121.0, 111.1, 67.6, 61.5, 60.2, 59.7, 57.0, 55.8, 53.8, 41.5, 36.1 ppm. Mass spectrum m/e 519 (p−1), 353, 262, 135, 91.

H. (1SR, 2SR, 3RS, 4R)-1-aza-2-diphenylmethyl-3-(2-methoxybenzamido)bicyclo[2.2.1]heptane The acylated product from above (68.6 mg, 0.132 mmol) (the product of Example 1G) was dissolved in methylene chloride and treated with 126.4 mg (1.252 mmol) triethylamine while the reaction mixture was cooled to 0° C. Slow dropwise addition of methanesulfonyl chloride (90.6 mg, 0.791 mmol) and reaction at 0° C. for 20 minutes provided the desired mesylate as judged by thin layer analysis (CH$_2$Cl$_2$, CH$_3$OH, NH$_4$OH; 94:5:1). The reaction mixture was diluted with 20 mL of aqueous saturated bicarbonate solution and the organic phase was washed with brine, dried over sodium sulfate, filtered and evaporated in vacuo. The mesylate was taken as an oil into 20 mL of ethanol and heated to reflux for 16 hours. The reaction mixture was then evaporated in vacuo and the residue was redissolved in methanol and treated with 68 mg of 10% palladium on carbon (Pd/C). The reaction mixture was hydrogenated at 45 psi for 1.5 hours then filtered and retreated with 70 mg of Pd/C and rehydrogenated under 45 psi hydrogen for 1 hour. The reaction was filtered through Celite® and the methanol was removed in vacuo. The residue was treated with 30 mL of saturated bicarbonate solution and extracted with 3×10 mL of methylene chloride. The organic layer was dried and evaporated. The residue was chromatographed on silica gel eluting with CH$_2$Cl$_2$, CH$_3$OH, NH$_4$OH (98:1:1) to afford 29 mg (53%) of the desired azabicyclic structure.

$^1$H NMR (CDCl$_3$, 250 MHz) δ8.02–7.99 (d, 1H, J=9.4 Hz), 7.88–7.84 (dd, 1H, J=7.7 Hz, J=1.8 Hz), 7.44–6.86 (m, 12H), 4.45–4.39 (t, 1H, J=7.2 Hz), 4.03 (s, 3H), 3.85–3.70 (m, 2H), 2.87–2.75 (m, 1H), 2.69–2.51 (m, 3H), 2.38–2.34 (d, 1H, J=10.4 Hz), 1.76–1.64 (m, 1H), 1.46–1.36 (m, 1H) ppm.

$^{13}$C NMR (CDCl$_3$, 62.9 MHz) δ163.6, 156.9, 144.7, 142.7, 132.3, 132.2, 128.4, 128.3, 127.9, 127.1, 126.0, 125.8, 121.1, 110.9, 72.2, 56.0, 55.8, 55.7, 54.9, 52.7, 44.6, 27.1 ppm. Mass spectrum m/e 412 (p+), 277, 222, 135, 91.

I. (1SR, 2SR, 3SR, 4RS)-1-aza-2-diphenylmethyl-3-(2-methoxyphenyl)methylaminobicyclo[2.2.1]heptane To a solution of 29 mg (0.070 mmol) of the material from the previous step (the product of Example 1H) in 4 mL of dry THF at 0° C. was added 351 μL (0.351 mmol) 1M borane in THF dropwise over 1 min. The reaction was then heated to reflux for a period of 3 hours. The reaction mixture was cooled to room temperature and an additional equivalent (70 μL) of borane-THF complex was added. The reaction was reheated to reflux for a period of 1.5 hours. The reaction mixture was cooled to room temperature and was quenched by the careful addition of 117 μL 6N HCl. The quenched reaction was heated under reflux for 10 min and the cooled to room temperature. The mixture was made basic with 2N NaOH and extracted with ethyl acetate (2×15 mL). The organic phase was dried and evaporated. The residue was chromatographed on silica gel using $CH_2Cl_2$, $CH_3OH$, $NH_4OH$ (97:2:1) to afford 17 mg (61%) of the desired material.

$^1$H NMR (CDCl$_3$, 250 MHz) δ7.31–7.05 (m, 12H), 6.83–6.70 (m, 2H), 4.21–4.17 (d, 1H, J=12.1 Hz), 3.71–3.67 (d, 1H, J=13.7 Hz), 3.55 (s, 3H), 3.54–3.45 (m, obs, 1H), 3.45–3.39 (d, 1H, J=13.7 Hz), 3.09–3.05 (d, 1H, J=9.8 Hz), 2.74–2.64 (m, 3H), 2.47–2.43 (m, 1H), 2.18–2.15 (d, 1H, J=9.9 Hz), 1.68–1.50 (m, 1H), 1.09–1.04 (m, 1H) ppm.

$^{13}$C NMR (CDCl$_3$, 62.9) δ157.3, 129.3, 128.9, 128.4, 127.8, 127.7, 127.3, 126.2, 125.8, 119.9, 109.8, 72.0, 63.6, 56.1, 55.1, 54.8, 50.8, 47.2, 41.4, 26.9 ppm.

Mass spectrum m/e 399 (p+1), 231, 121.

The dihydrochloride salt was prepared by treatment of the free base with saturated HCl (g) in ether. The solid was allowed to granulate overnight to afford 10 mg white solid. M.P. −211° C. (decomp).

EXAMPLE 2

[1SR, 2SR, 3SR, 4RS]-1-aza-2-phenyl-3-(2-methoxyphenyl)methylaminobicyclo[2.2.1]heptane A. (2SR, 3RS, 4RS)-1N-phenylmethyl-2-phenyl-3-nitro-4-carbomethoxymethyl pyrrolidine A solution of nitrostyrene (3.09 g, 20.73 mmol) (25 trans-B-nitrostyrene from Aldrich) and 5.00 g (22.8 mmol) of previously prepared methyl-4-phenylmethylamino-2-butenoate (the product of Example 1A) in 250 mL methanol was stirred at room temperature for 16 hours. The reaction mixture was evaporated in vacuo and the residue was chromatographed on silica gel with 9/1 hexane/ethyl acetate. There was obtained 7.4 g (100%) of the desired material as a single isomer.

$^1$H NMR (CDCl$_3$, 250 MHz) δ7.5–7.23 (m, 10 H), 5.02–4.97 (dd, 1H, J=8.4 Hz, J=4.5 Hz), 4.32–4.31 (d, 1H, J=4.5 Hz), 3.93–3.88 (d, 1H, J=13.1 Hz), 3.65 (s, 3H), 3.43–3.37 (d, 1H, J=13.1 Hz), 3.29–3.23 (t, 1H, J=6.8 Hz), 3.17–3.07 (m, 1H), 2.57–2.50 (t, 1H, J=9.5 Hz), 2.43–2.41 (d, 2H, J=7.4 Hz) ppm.

$^{13}$C NMR (CDCl$_3$, 62.9 MHz) δ171.4, 139.8, 128.9, 128.6, 128.4, 128.3, 127.3, 127.2, 95.2, 73.0, 57.4, 56.5, 51.9, 37.6, 32.1 ppm.

IR (CHCl$_3$) λ1737, 1546, 1376 cm$^{-1}$.

Mass spectrum m/e 353 (p−1), 308, 234, 91.

B. (2SR, 3SR, 4RS)-1N-phenylmethyl-2-phenyl-3-nitro-4-carbomethoxymethyl pyrrolidine A solution of 780 mg (2.2 mmol) of the previous product (the product of Example 2A) in 10 mL of ether was treated with 100 mg (0.66 mmol) of 1,8-diazabicyclo[5.4.0]undec-7-ene. The reaction mixture was seeded or scratched to induce crystallization and after 2 hours a white sol].id was filtered and dried to afford 482 mg of the desired product. The mother liquor was allowed to stir for 16 hours whereupon an additional 46 mg was obtained (total yield 68%).

$^1$H NMR (CDCl$_3$, 250 MHz) δ7.47–7.25 (m, 10 H), 5.09–5.03 (dd, 1H, J=8.5 Hz, J=5.2 Hz), 4.02–3.98 (d, 1H, J=8.5 Hz), 3.93–3.88 (d, 1H, J=13.3 Hz), 3.65 (s, 3H), 3.52–3.41 (m, 2H, 3.09–3.03 (d, 1H, J=13.3 Hz), 2.55–2.50 (m, 2H), 2.09–2.02 (m, 1H) ppm.

IR (CHCl$_3$) λ1737, 1553, 1377 cm$^{-1}$.

Mass spectrum m/e 354 (p+) 308 (p−46), 234, 91.

C. (2SR, 3SR, 4RS)-1N-phenylmethyl-2-phenyl-3-amino-4-(2-hydroxyethyl) pyrrolidine A solution of 464 mg (1.31 mmol) of the compound prepared above was dissolved in 50 mL of methanol and was treated with 1.2 g of (water washed) RaNi (pH 7) stored under ethanol. The mixture was placed in a Parr pressure bottle and placed under 50 psi hydrogen for a period of approximately 4 hours. The reaction mixture was purged with nitrogen and then filtered. The filtrate was evaporated in vacuo and the residue (426 mg) was used directly in the next step.

$^1$H NMR (CDCl$_3$, 300 MHz) δ7.40–7.21 (m, 10 H), 3.92–3,87 (d, 1H, J=13.3 Hz), 3.63 (s, 3H), 3.61–3.59 (d, 1H, J=7.1 Hz), 3.32–3.27 (dd, 1H, J=9.3 Hz, J=7.1 Hz), 3.11–3.06 (m, obs, 1H), 3.06–3.02 (d, 1H, J=13.3 Hz), 2.68–2.60 (dd, 1H, J=15.6 Hz, J=6.0 Hz), 2.43–2.35 (dd, 1H, J=15.6 Hz, J=8.6 Hz), 2.32–2.11 (m, 1H), 1.93–1.87 (t, 1H, J=9.3 Hz).

$^{13}$C NMR (CDCl$_3$, 75.5 MHz) δ173.5, 139.4, 139.5, 128.8, 128.6, 128.5, 128.2, 127.4, 126.9, 73.3, 60.7, 58.4, 57.8 51.6, 43.1, 37.6 ppm.

Mass spectrum m/e 324 (p+), 307, 233, 118, 91.

IR (CHCl$_3$) λ1733 cm$^{-1}$.

A solution of lithium aluminum hydride was prepared by dilution of 3.57 mL of 1M reagent THF with 45 mL of anhydrous THF. The solution was cooled to 0° C. and was treated with 579 mg (1.79 mmol) of material derived from several runs of previous step (the penultimate product of Example 2C) in 8 mL THF. The reaction mixture was stirred for 60 min at 0° C. The reaction was quenched by the sequential addition of 135 μL water, 135 μL 15% aqueous sodium hydroxide and 405 μL water. The resultant precipitate was granulated for 15 min and the slurry was filtered through Celite®. The residue after evaporation was chromatographed on 'silica gel eluting with $CH_2Cl_2$, $CH_3OH$, $NH_4OH$ (97:2:1) to afford 380 mg of the desired product (72%).

$^1$H NMR (CDCl$_3$, 300 MHz) δ7.43–7.24 (m, 10H), 3.89–3.84 (d, 1H, J=13.1 Hz), 3.76–3.56 (m, 3H), 3.25–3.22 (d, 1H, J=8.3 Hz), 3.18–3.13 (d, 1H, J=13.2 Hz), 3.08–3.02 (dd, 1H, J=8.8 Hz, J=6.0 Hz), 2.28 (s, 1H), 2.06–1.98 (dd, 1H, J=10.7 Hz, J=8.9 Hz), 1.83–1.56 (m, H) ppm.

Mass spectrum m/e 296 (p+), 279, 209, 188, 118, 91.

D. (2SR, 3SR, 4RS)-1N-phenylmethyl-2-phenyl-3-(2-methoxyphenyl)methylamino-4-(2-hydroxyethyl)-pyrrolidine A solution of 320 mg (1.08 mmol) of material from the previous step (the final product of Example 2C) in 30 mL of acetic acid was treated with 3Å molecular sieves, 126 mg (0.928 mmol) anisaldehyde (Aldrich) and 328 mg (1.55 mmol) sodium triacetoxyborohydride. The reaction mixture was stirred for 16 hours and was then evaporated in vacuo. The residue: was partitioned between 1N HCl and ether (50 mL). The aqueous layer was made basic to pH 12 and then was extracted with ethyl acetate. After drying and evaporation there was obtained 265 mg (59%) of the desired diamine.

$^1$H NMR (CDCl$_3$, 300 MHz) δ7.53–7.10 (m, 11H), 6.75–6.68 (m, 2H), 6.54–6.52 (d, 1H, J=7.3 Hz), 3.95–3.92 (d, 1H, J=8.8 Hz), 3.78–3.74 (d, 1H, J=13.1 Hz), 3.63 (s, JH), 3.54–3.47 (t, 1H, J=9.9 Hz), 3.35–3.11 (m, 3H), 3.05–2.95 (m, 1H), 2.11 (m, 2H), 1.79–1.70 (m, 1H), 1.60–1.49 (m, 1H) ppm.

$^-$C NMR (CDCl$_3$, 75.5 MHz) δ157.5, 140, 138.5, 130.1, 129.8, 128.7, 128.5, 128.4, 128.1, 127.6, 126.8, 120.3, 110.1, 71.4, 67.3, 62.1, 58.2, 57.3, 55.0, 47.2, 46.3, 35.7 ppm.

Mass spectrum m/e 416 (p+), 325, 280, 209, 188, 118, 91.

E. (2SR, 3SR, 4RS)-2-phenyl-3-(2-methoxyphenylmethyl)amino-4-(2-hydroxyethyl)pyrrolidine A solution of 200 mg (0.48 mmol) of the previously prepared compound (the product of Example 2D) in methanol (50 mL) was treated with 5 mL of HCl (g) in methanol. The solution was treated with 5 mg of 10% palladium on carbon and placed under an atmosphere of 45 psi hydrogen. The reaction was hydrogenated for 4 hours and was then treated with a further quantity of catalyst (15 mg) and hydrogenated for 16 hours. The catalyst was removed by filtration and the methanol was evaporated in vacuo. The residue was partitioned between ethyl acetate and 1N NaOH (aq). The organic phase was then dried and evaporated to an oil. The product was chromatographed on silica gel eluting with $CH_2Cl_2$, $CH_3OH$, $NH_4OH$ (94:5:1)to yield 95 mg (61%) of the desired product.

$^1$H NMR (CDCl$_3$, 250 MHz) δ7.39–7.14 (m, 6H), 6.89–6.73 (m, 3H), 4.60–4.57 (d, 1H, J=7.6 Hz), 3.74–3.65 (m, obs, 5H), 3.65 (s, 3H), 3.58–3.51 (m, 2H), 3.45–3.38 (dd, 1H, J=10.1 Hz, J=7.9 Hz), 3.21–3.14 (dd, 1H, J=9.9 Hz, J=7.7 Hz), 2.81–2.73 (t, 1H, J=10.0 Hz), 2.19–2.00 (m, 1H), 1.91–1.82 (m, 1H), 1.7–1.51 (m, 1H) ppm.

$^{13}$C NMR (CDCl$_3$, 62.9 MHz) δ157.4, 141.6, 130.1, 128.6, 128.5, 128.3, 127.4, 126.8, 120.4, 110.1, 67.7, 64.2, 62.2, 54.9, 51.5, 47.4, 45.0, 36.1 ppm.

Mass spectrum m/e 327 (p+1), 208, 118, 91.

F. (1SR, 2SR, 3SR, 4RS)-1-aza-2-phenyl-3-(2-methoxyphenyl)methylaminobicyclo[2.2.1]heptane The product of Example 2E from the previous step (83 mg, 0.25 mmol) was converted to the dihydrochloride after dissolution in HCl saturated methylene chloride followed by evaporation. This material was redissolved in 7 mL of methylene chloride and treated with 278 μL (3.81 mmol) of thionyl chloride and the reaction mixture was stirred for 16 hours. The solvent was removed in vacuo and the yellow solids were triturated with ether (91 mg crude weight). This material was dissolved in 15 mL of dry acetonitrile and treated with 155 mg (1.02 mmol) (1,8-diazabicyclo[5.4.0] undec-7-ene from Aldrich) DBU and stirred for 16 hours. The reaction mixture was evaporated in vacuo. The residue was chromatographed on silica gel eluting with $CH_2Cl_2$, $CH_3CH_2OH$, $NH_4OH$ (97:2:1). There was obtained 15 mg of desired product (20%).

$^1$H NMR (CDCl$_3$, 250 MHz) δ7.34–7.17 (m, 6H), 7.08–7.05 (dd, 1H, J=7.3 Hz, J=1.7 Hz) , 6.91–6.81 (m, 2H), 3.86–3.80 (d, 1H,. J=14.0 Hz), 3.76–3.73 (d, obs, 1H), 3.73 (s, 3H), 3.59–3.53 (d, 1H, J=14.0 Hz), 3.10–3.06 (d, 1H, J=9.5 Hz), 2.94–2.80 (m, obs, 1H), 2.83–2.81 (d, 1H, J=6.4 Hz), 2.63–2.61 (d, 1H, J=4.5 Hz), 2.62–2.55 (m, obs, 1H) , 2.44–2.40 (d, 1H, J=9.5 Hz) , 1.78–1.67 (m, 1H), 1.2–1.11 (m, 1H) ppm.

$^{13}$C NMR (CDCl$_3$, 62.9 MHZ) δ157.5, 138.7, 129.7, 128.0, 127.0, 126.3, 120.1, 109.9, 71.9, 64.0, 57.0, 55.9, 54.9, 48.5, 41.6, 39.5, 26.9 ppm.

Mass spectrum m/e 308 (p+), 252, 187, 121, 91.

HRMS calc'd for $C_{20}H_{24}N_2O$: 308.1883. Found: 308.1889.

This material was dissolved in ether and treated with HCl/ether to provide a white solid which was recrystallized in methanol/ether to afford 10 mg of the dihydrochloride salt. M.p.=218° C.

EXAMPLE 3

(1SR, 2SR, 4RS)-1-aza-2-diphenylmethyl-3-[(2-methoxy-5-(1-dimethylethyl)phenyl)methylamino]-bicyclo[2.2.1]heptane A. (2SR, 3SR, 4RS)-1N-phenylmethyl-2-diphenylmethyl-3-(1,1-dimethylethoxycarbonylamido)-4-(2-hydroxyethyl)-pyrrolidine A solution of 10 gm (25.87 mmol) (2SR, 3SR, 4RS)-1N-phenylmethyl-2-diphenylmethyl-3-amino-4-(2-hydroxyethyl)pyrrolidine (prepared earlier) (the product of Example 1F) in 130 ml chloroform and 130 ml water was treated with 2.17 g (25.87 mmol) sodium bicarbonate and 5.65 g (25.87 mmol) di-tertbutyldicarbonate (Alrich). The reaction mixture was heated under reflux for 90 min and then allowed to cool to room temperature. The organic layer was separated and washed with brine. The solution was dried with sodium sulfate and evaporated in vacuo. There was obtained 12.3 g (100%). This material was used directly in the next step.

Mass Spectrum m/e 487 (p$^{+1}$), 431 (p-t-Bu).

IR (CHCl$_3$)3436, 1704, 2923, 1488, 1158 cm$^{-1}$.

B. (1SR, 2SR, 3SR, 4RS)-1-aza-2-diphenylmethyl-3-(1,1-dimethylethoxycarbonylamido)bicyclo[2.2.1]heptane A solution of 12.3 gm (25.87 mmol) of the compound previously prepared (the product of Example 3A) in 150 ml of methylene chloride was treated with 24.87 gm (245.78 mmol) triethylamine and the reaction was cooled to 0° C. The solution was treated with 17.78 gm ( 155.23 mmol) methanesulfonyl chloride dropwise over 10 minutes. After the addition was complete, a precipitate was formed. Thin layer analysis (94:5:1; $CH_2Cl_2$, MeOH, $NH_4OH$) indicated the reaction was complete 10 minutes after the addition was complete. The crude mesylate was processed by dilution of the reaction mixture with 300 ml of saturated aqueous bicarbonate. The organic phase was washed with aqueous brine and then was dried and evaporated. The residue was taken up in 250 ml of ethanol and the resulting solution was heated under reflux for 16 hours.

The reaction mixture was allowed to cool to room temperature and then transferred to a 500 ml Parr bottle. The solution was treated with 6 g of 10% palladium on carbon and placed under 47 psi hydrogen pressure for a period of 1 hour. At this point the reaction mixture was filtered and fresh catalysts (7.4 gm) was placed together with the reaction mixture into a Parr bottle and further hydrogenated for 2 hours. The reaction mixture was filtered and the filtrate was treated with 7 gm of fresh catalyst and hydrogenated overnight under 45 psi hydrogen gas. The reaction mixture was filtered through Celite® and the filtrate was evaporated in vacuo. The residue was partioned between saturated aqueous bicarbonate solution and methylene chloride. The organic phase was treated with saturated brine, dried and evaporated in vacuo. The residue was slurried in hexane to afford a white solid which amounted to 2.0 gm after filtration. The catalyst from the hydrogenations were slurried in methanol and water (5:3)for a period of 1 hour. The mixture was filtered through Celite® and the methanol was removed in vacuo. The resulting aqueous phase was extracted with methylene chloride, and the organic phase was dried with sodium sulfate and evaporated. The residue was taken up in methanol (600 ml) and treated with 7.5 gm of 10% palladium on carbon. The mixture was hydrogenated under 45 psi hydrogen for 2 hours and was filtered through Celite® and then evaporated in vacuo. The residue was partioned between 500 ml of saturated aqueous bicarbonate solution and methylene chloride (3×125 ml). The organic phase was washed with 300 ml of saturated aqueous brine solution, dried and evaporated. The residue was slurried in 200 ml of hexane to afford a white solid amounting to 3.05 gm. The total yield of the desired material was 5.05 gm (52%).

C. (1SR, 2SR, 3SR, 4RS)-1-aza-2-diphenylmethyl-3-aminobicyclo[2.2.1]heptane-dihydrochloride A solution of the previous compound (2.79 gm, 7.37 mmol) (the product of Example 3B) in 125 ml of dioxane was treated with 250 ml of ethyl acetate saturated with HCl gas. The reaction mixture was heated to 50° C. whereupon a precipitate began to form. The mixture was heated for 2 hours and then allowed to cool to room temperature. The mixture was filtered and the solids were washed with ether. There was obtained 2.6 gm (100%) of the desired product as the dihydrochloride salt. This material was converted to the free base for analysis.

$^{13}$C NMR (CDCl$_3$, 62.90 MHz) δ128.9, 128.5, 127.7, 127.4, 126.3, 125.9, 73.0, 57.7, 55.8, 54.6, 51.1, 46.1, 27.3 ppm.

D. (1SR, 2SR, 3SR, 4RS)-1-aza-2-diphenylmethyl-3-[(2-methoxy-5-(1,1-dimethylethyl)phenylmethylene]aminobicyclo[2.2.1]heptane The dihydrochloride (110 mg, 0.313 mmol) from the previous step was partioned between 12% aqueous sodium hydroxide and methylene chloride. The organic phase was washed with brine solution, dried over sodium sulfate and evaporated in vacuo to afford 82 mg (0.295 mmol) of the corresponding free base. This material was dissolved in toluene (35 ml) and was treated with 57 mg (0.295 mmol) of 2-methoxy-5-(11-dimethylethyl)benzaldehyde (preparing according to the procedure described by W. E. Smith in the *Journal of Organic Chemistry*, Vol. 37, No. 24, p. 3972 (1972), ultimately starting from the known and readily available 4-(tert-butyl)phenol (Aldrich)). The reaction mixture was heated under reflux over a Dean-Stark trap for 2.5 hours. Analysis of the NMR spectrum from a small reaction aliquot indicated product formation was complete. The solution was evaporated in vacuo to provide the imine as a crude oil which was used directly in the next step without purification.

$^1$H NMR (CDCl$_3$, 250 MHz) δ7.98 (s, 1H), 7.79 (d, 1H, J=3.5 Hz), 7.4–6.7 (m, 13H), 4.25 (d, 1H, J=12.8 Hz), 3.91 (s, 1H), 3.7 5.7 Hz), 2.93–2.79 (m, 1H), 2.7–2.55 (m, 1H), 2.34 (dd, 1H, J=5.7 Hz, J=9.2 Hz), 1.72–1.61 (obsc-m, 1H), 1.3–1.2 (m, 1H), 1.39 (s, 9H) ppm E. (1SR, 2SR, 3SR, 4RS)-1-aza-2-diphenylmethyl-3-[(2-methoxy-5-(1,1-dimethylethyl)phenyl)methylamino]bicyclo[2.2.1]heptane The crude imine from the above step (the product of Example 3D) was taken into 20 ml of dichloroethane and treated with 87 mg (0.412 mmol) of sodium triacetoxyborohydride. The mixture was stirred overnight (16 hours). Thin layer analysis (CH$_2$Cl$_2$:MeOH:NH$_4$OH; 94:5:1)indicated the reaction was complete. Reaction quenching with 20 ml of saturated aqueous bicarbonate solution was followed by dilution with methylene chloride, extraction and drying. The organic phase was evaporated in vacuo to afford 128 mg of an oil. The dihydrochloride salt was formed after dissolution of the free base in ether and treatment with saturated HCl gas also in ether. The crude salt was obtained by direct evaporation of this reaction mixture. The residue was taken up in methanol (3 ml), filtered and treated with ether until the cloud point. The mixture was stirred overnight whereupon crystallization occurred. The resulting solid was isolated in 79% overall yield (123 mg).

Anal. Calc'd for C$_{31}$H$_{38}$N$_2$O·2HCl·H$_2$O C; 68.25, H; 7.76, N; 5.13 found C; 68.48, H; 7.94, N; 5.08.

The title compounds of Examples 4–8 were prepared by the previous two step procedure from (1SR, 2SR, 3SR, 4RS)-1-aza-2-diphenylmethyl-3-aminobicyclo[2.2.1]heptane-dihydrochloride using the appropriate aldehyde reagent of choice in each instance.

EXAMPLE 4

(1SR, 2SR, 3SR, 4RS)-1-aza-2-diphenylmethyl-3-[(2-methoxyphenyl) methylamino]bicyclo[2.2.1]heptane $^1$H NMR (CDCl$_3$, 250 MHz) δ7.31–7.05 (m, 12H), 6.83–6.70 (m, 2H), 4.21–4.17 (d, 1H, J=12.1 Hz), 3.71–3.67 (d, 1H, J=13.7 Hz) , 3.55 (s, 3H) , 3.54–3.45 (m, obs, 1H), 3.45–3.39 (d, 1H, J=13.7 Hz), 3.09–3.05 (d, 1H, J=9.8 Hz), 2.74–2.64 (m, 3H), 2.47–2.43 (m, 1H), 2.18–2.15 (d, 1H, J=9.9 Hz), 1.68–1.50 (m, 1H), 1.09–1.04 (m, 1H)ppm.

$^{13}$C NMR (CDCl$_3$, 62.9) δ157.3, 129.3, 128.9, 128.4, 127.8, 127.7, 127.3, 126.2, 125.8, 119.9, 109.8, 72.0, 63.6, 56.1, 55.1, 54.8, 50.8, 47.2, 41.4, 26.9 ppm.

Mass spectrum m/e 399 (p+1), 231, 121.

EXAMPLE 5

(1SR, 2SR, 3SR, 4RS)-1-aza-2-diphenylmethyl-3-[(2-methoxy-5-(1-methylethane)phenyl)methylamino]bicyclo-[2.2.1]heptane Mass spectrum m/e (p$^+$), 273 (p-(C$_6$H$_5$)$_2$CH$_2$—).
IR (CHCl$_3$)3323, 2932, 1600, 1450, 904 cm$^{-1}$.

EXAMPLE 6

(1SR, 2SR, 3SR, 4RS)-1-aza-2-diphenylmethyl-3-[(2-methoxy-5-(1-methylpropane)phenyl)methylamino]bicyclo-[2.2.1]heptane Mass spectrum (FAB) 455 (p$^+$).

EXAMPLE 7

(1SR, 2SR, 3SR, 4RS)-1-aza-2-diphenylmethyl-3-[(2-methoxy-5-trifluoromethoxyphenyl)methylamino]bicyclo[2.2.1]heptane IR (CHCl$_3$ λ3328, 2934, 1600, 1450, 1257, 1157, 904 cm$^{-1}$;

Anal. calc'd for C$_{28}$H$_{31}$N$_2$O$_2$F$_3$Cl$_2$: C, 60.55; H, 5.62; N, 5.04; Found C, 60.23; H, 5.80; N, 4.94.

EXAMPLE 8

(1SR, 2SR, 3SR, 4RS)-1-aza-2-diphenylmethyl-3-[(2-methoxy-4,5--dimethylphenyl)methylamino]bicyclo[2.2.1]heptane $^1$H NMR (CDCl$_3$, 250 MHz) δ7.34–7.06 (m, 10H), 6.53 (s, H), 6.43 (s, 1H), 4.22–4.18 (d, 1H, J=12.1 Hz), 3.65–3.36 (dd, 2H, J=13.4 Hz), 3.54 ( s, 3H) , 3.53–3.45 (dd, 1H, J=12.3 Hz, J=6.9 Hz), 3.09–3.06 (d, 1H, J=9.7 Hz), 2.79–2.66 (m, H) , 2.48–2.39 (m, 1H), 2.23 (s, 3H), 2.18 (s, 1H), 2.14 (s, H) , 1.69–1.57 (m, 1H), 1.13–1.03 (m, 1H) ppm.

$^{13}$C NMR (CDCl$_3$, 62.9 MHz) δ1.55.5, 145.9, 143.9, 135.7, 130.6, 128.9, 128.4, 127.7, 127.6, 127.4, 126.2, 125.8, 125.0, 111.6, 72.1, 63.7, 56.1, 55.3, 54.8, 50.8, 46.8, 41.4, 26.9, 19.9, 18.6 ppm.

EXAMPLE 9

(1SR, 2SR, 3RS, 4RS)-1-aza-2-phenyl-3-(2-methoxy-5-trifluoromethoxyphenyl)methylaminobicyclo[2.2.1]heptane A. (2SR, 3RS, 4RS)-1N-phenylmethyl-2-phenyl-3-nitro-4-(2-hydroxyethyl) pyrrolidine)

To a flame dried flask containing borane—THF complex (11.3 ml, 11.3 mmol) in 50 ml of dry THF at 0° C. was added 1.0 gm (2.82 mmol) of (2SR, 3RS, 4RS)-1-N-phenylmethyl-2-phenyl-3-nitro-4-carbomethoxymethylpyrrolidine (the product of Example 2A) in 30 ml of dry THF in a dropwise manner. During the addition, gas evolution was noticed and the reaction mixture became cloudy. To this solution was added 53 mg (1.4 mmol) sodium borohydride; the resultant mixture was allowed to warm to room temperature and was then heated to reflux for 1.5 hours. Thin layer analysis (30% ethyl acetate in hexane) indicated the reaction had proceeded to a mixture of borane complexes. The reaction was allowed to cool to room temperature and was then treated with 10 ml of 6N HCl and reheated to reflux for 1 hour. The reaction mixture was partioned between 100 ml water and 50 ml of methylene chloride and under cooling and stirring aqueous base was added until pH 13 was reached. The organic phase was washed with brine, dried and evaporated in vacuo to afford a crude oil. Chromatography on silica gel (30% ethyl acetate in hexane) afforded 552 mg (60%) of the desired nitro-alcohol product.

B. (2SR, 3RS, 4RS)-1-N-phenylmethyl-2-phenyl-3-amino-4-(2-hydroxyethyl) pyrrolidine A solution of the previously prepared compound (0.9 gm, 2.75 mmol) (the product of Example 9A) in 40 ml of methanol was treated with 1.2 g of Raney nickel which had been previously washed with water until the washings were neutral. The mixture was hydrogenated under 48 psi hydrogen pressure for 16 hours. At this point, the reaction mixture was filtered through celite and the filtrate was evaporated in vacuo. Chromatography on silica gel (elution with CH$_2$Cl$_2$: MeOH: NH$_4$OH; 97:3:1)afforded 512 mg (62%) of the desired product.

C. (25R, 3RS, 4RS)-1N-phenylmethyl-2-phenyl-3-[(1,1-dimethylethoxy)carbonylamino]-4-(2-hydroxyethyl)-pyrrolidine A solution of 133 mg (0.45 mmol) of the previously prepared compound was taken up in 1 ml of chloroform and a solution of 37.8 mg (45 mmol) sodium bicarbonate in water. To the rapidly stirred mixture was added 98.2 mg (45 mmol) of di-t-butyldicarbonate and the resulting mixture was heated to reflux for 1.5 hours. The reaction wa diluted with methylene chloride and water. The organic phase was separated, dried and evaporated to afford a crude oil which was chromatographed on silica gel (elution with CH$_2$Cl$_2$: MeOH: NH$_4$OH; 97:3:1)to afford 145 mg (81%) of the desired product.

D. (1SR, 2SR, 3RS, 4RS)-1-aza-2-phenyl-3-[(1,1-dimethylethoxy)carbonylamino]bicyclo[2.2.1]heptane A solution of the previously prepared compound (178 mg, 0.449 mmol) (the product of Example 9C) in methylene chloride was treated with 595 μl (4.27 mmol) triethylamine and the solution was cooled to 0° C. before the addition of methanesulfonylchloride (210 μl, 2.70 mmol). After addition was complete, the reaction mixture was allowed to warm to room temperature and was then partitioned between 20 ml of saturated aqueous bicarbonate solution and 20 ml of methylene chloride. The organic phase was washed with brine solution and then dried and evaporated. The residue was taken directly into 60 ml of methanol and heated to reflux for 16 hours. At this point, the reaction mixture was allowed to cool to room temperature and was placed in a 250 ml Parr bottle, treated with 150 mg of 10% palladium on carbon and hydrogenated under 48 psi hydrogen gas for 1 hour. The catalyst was removed via filtration, 150 mg catalyst was charged and hydrogenation was continued for a period of 4 hours. The catalyst was removed via filtration through celite and the filtrate was evaporated in vacuo. The residue was partitioned between methylene chloride and saturated aqueous bicarbonate solution. The organic phase was dried and evaporated in vacuo to afford an oil. Chromatography on silica gel (elution with CH$_2$Cl$_2$:MeOH:NH$_4$OH; 97:3:1) afforded 35 mg (28%) of the more polar material which was the desired product.

E. (1SR 2SR 3RS 4RS)-1-aza-2-phenyl-3-aminobicyclo[2.2.1]heptane-dihydrochloride The compound (35 mg, 122 mmol) from the previous step (the product of Example 9D) was dissolved in 1 ml of ethyl acetate and was added to a cold (0° C.) solution of HCl (g) in 5 ml of ethyl acetate. After 2 hours, the reaction mixture was evaporated in vacuo and the powdery residue was dissolved in 10 ml of water and adjusted to pH 12 with sodium hydroxide solution. The aqueous mixture was extracted with methylene chloride and the organic phase was dried and evaporated. The residue was chromatographed on silica gel (elution with CH$_2$Cl$_2$:MeOH:NH$_4$OH; 95:4:1)to afford 17 mg (75%) of the desired product.

F. (1SR, 2SR, 3RS, 4RS)-1-aza-2-phenyl-3-[(2-methoxy-5-trifluoromethoxyphenyl)methylamino]bicyclo[2.2]heptane The compound (17 mg, 0.090 mmol) from the previous step (the product of Example 9E) was dissolved in 3 ml of dichloroethane along with 20 mg (0.090 mmol) of 2-methoxy-5-trifluoromethoxybenzaldehyde (prepared according to the procedure described by W. E. Smith in the *Journal of Organic Chemistry*, Vol. 37, No. 24, p. 3972 (1972), ultimately starting from the known and readily available α, α, α-trifluoro-p-cresol(Aldrich)) and 27 mg (0.130 mmol) sodium triacetoxyborohydride. The mixture was stirred for 16 hours at room temperature and was then partitioned between methylene chloride and 2 N HCl. The aqueous phase was adjusted to pH 13 and repeatedly extracted with methylene chloride. The combined organics were dried and evaporated. The residue was chromatographed on silica gel (elution with CH$_2$Cl$_2$:MeOH:NH$_4$OH;95:5:1) to afford 17 mg (48%) of the desired product.

$^{13}$C NMR (CDCl$_3$, 62.9 MHz) δ155.9, 129.8, 128.4, 126.6, 125.6, 122.7, 120.7, 110.7, 73.8, 68.1, 57.7, 55.6, 55.2, 48.3, 41.0, 20.7 ppm; mass spectrum m/e 392 (p$^+$), 260, 205, 187; HRMS m/e Calc'd for C$_{21}$H$_{23}$F$_3$N$_2$O$_2$: 392.1710; found: 392.17242;

Redissolution of the above compound in ether (20 ml) with 2 drops of methanol followed by treatment with a solution of HCl (g) in ether afforded a semi-solid dihydrochloride salt. The solvent was then removed in vacuo and the gummy residue was taken up in i-propanol, filtered and the filtrate crystallized by the addition of ether. There was obtained 12 mg of the desired dihydrochloride salt. M.p. 203° C.

EXAMPLE 10

(2SR, 3SR, 4RS)-2-diphenylmethyl-3-[(2-methoxyphenyl)-methylamino]-4-(2-hydroxyethyl) pyrrolidine A. (2SR, 3SR, 4RS)-N-1-phenylmethyl-2-diphenylmethyl-3-[(2-methoxyphenyl)methylamino]-4-(2-hydroxyethyl) pyrrolidine A solution of 500 mg (1.29 mmol) (2SR, 3SR, 4RS)-N-1-phenylmethyl-2-diphenylmethyl-3-amino-4-(2-hydroxyethyl)-pyrrolidine was dissolved in 60 ml of dichloroethane and treated with 176 mg (1.29 mmol) anisaldehyde. To the solution was added 384 mg (1.81 mmol) sodium triacetoxyborohydride and the reaction mixture was allowed to stir overnight. The reaction mixture was quenched by the addition of 20 ml of saturated aqueous bicarbonate solution and methylene chloride. The organic phase was washed with brine, dried and evaporated in vacuo. The resultant oil was chromatographed on silica gel with $CH_2Cl_2$: MeOH: $NH_4OH$; 97:2:1 to afford 500 mg of pure product. The residue after evaporation was redissolved in methanol (containing a few drops of methylene chloride to improve solubility) and treated with HCl (g) in methanol. The dihydrochloride salt was isolated by evaporation of the reaction mixture and redissolution in methanol followed by addition of enough ether to initiate cloud formation. After 2–3 hours of stirring the precipitate was filter to afford 475 mg (63%) of the above titled product as the dihydrochloride salt.

Mass spectrum m/e 339 (p-$C_6H_5$)$_2$CH—), 121,91.

IR ($CHCl_3$)2895, 2835, 1600, 1448 $cm^{-1}$.

B. (2SR, 3SR, 4RS)-2-diphenylmethy-3-[(2-methoxyphenyl)methylamino]-4-(2-hydroxyethyl)pyrrolidine A solution of 340 mg (0.587 mmol) of the above described product as the dihydrochloride (the product of Example 10A) in 50 ml of methanol was added to a Parr bottle containing 36 mg of 10% palladium on carbon with 10 ml of methanol saturated with HCl gas. The mixture was placed under 45 psi hydrogen pressure and hydrogenated overnight (16 hours). The reaction mixture was filtered and evaporated in vacuo. The residue was treated with saturated aqueous bicarbonate solution and extracted with methylene chloride. The organic phase was dried with sodium sulfate and evaporated. The residue was chromatographed on silica gel to afford 70 mg of clean product (elution with $CH_2Cl_2$: MeOH: $NH_4OH$; 94:5:1). The dihydrochloride salt was prepared in ether—methanol (5:1) and was isolated by direct filtration of the reaction mixture.

$^{13}C$ NMR ($CDCl_3$, 75.5 MHz) δ157.5, 143.5, 143, 129.5, 128.7, 128.7, 128.3, 128.1, 128.0, 126.4, 120.4, 110.1, 64.6, 64.3, 61.6, 55.2, 51.8, 51.2, 46.2, 42.5, 37.4 ppm; mass spectrum m/e 417 ($p^{+1}$), 37, 328, 249.

EXAMPLE 11

(2SR, 3SR, 4RS)-2-diphenylmethyl-3-[(2-methoxy-5-(1,1-dimethylethane)phenyl)methylamino]-4-(2-hydroxyethyl) pyrrolidine A. (2SR, 3SR 4RS)-2-diphenylmethyl-3-amino-4-(2-hydroxyethyl)pyrrolidine A solution of 1.0 gm (2.59 mmol) (2SR, 3SR, 4RS)-N-1-phenylmethyl-2-diphenylmethyl-3-amino-4-(2-hydroxyethyl) pyrrolidine (the product of Example 1F) was dissolved in 50 ml of methanol and was treated with 75 ml of HCl—methanol and 100 mg of 10% palladium on carbon. The mixture was placed under 45 psi hydrogen pressure in a 250 ml Parr bottle for a period of 16 hours. The reaction was filtered through celite and evaporated to a white paste. The residue was treated with 100 ml of ether and the solids were granulated for 1 hour. There was obtained 960 g (100%) of the desired product as the dihydrochloride salt.

$^{13}C$ NMR ($D_2O$, 62.9 MHz) δ141.6, 140.0, 132.9, 132.7, 131.6, 130.1, 65.2, 62.3, 58.1, 51.1, 44.4, 35.8 ppm.

B. (2S, 3S, 4R)-2-diphenylmethyl-3-[(2-methoxy-5-(1,1-dimethylethane)phenyl)methylamino]-4-(2-hydroxyethyl)pyrrolidine The free base (81 mg, 0.273 mmol) of the previously described compound (the product of Example 11A) was dissolved in 25 ml of dichloroethane and treated with 53 mg (0.273 mmol) of 2-methoxy-5-(1,1-dimethylethane)benzaldehyde. The mixture was then treated with 87 mg (0.410 mmol) sodium triacetoxyborohydride and the reaction was stirred for 16–18 hours. Added 20 ml of saturated aqueous bicarbonate solution to the reaction mixture and separated the organic phase, washed with saturated aqueous brine solution, dried and evaporated. The crude product was chromatographed on silica gel eluting with $CH_2Cl_2$: MeOH: $NH_4OH$; 94:5:1 to afford 57 mg of the desired material. The dihydrochloride salt was prepared in ether—methanol (5:1). The salt was isolated by recrystallization-granulation in methanol-ether (1:20)for 16 hours. This afforded 45 mg of the desired dihydrochloride salt.

Free Base $^{13}C$ NMR ($CDCl_3$, 62.9 MHz) δ155.2, 143.7, 143.1, 142.9, 128.6, 128.5, 128.2, 127.3, 127.1, 126.4, 126.3, 124.7, 109.5, 64.8, 64.7, 61.5, 55.2, 51.6, 51.2, 47.5, 42.7, 37.3, 34.0, 31.5 ppm.

The title compounds of Examples 12–16 were prepared by the procedure described in Example 11B, starting from the appropriate aldehyde reagent of choice in each instance.

EXAMPLE 12

(2SR, 3SR, 4RS)-2-Diphenylmethyl-3-[(2-methoxy-5-(trifluoromethoxy)phenyl)methylamino]-4-(2-hydroxyethyl)-pyrrolidine $^{13}C$ NMR ($CDCl_3$, 62.9 MHz) δ155.7, 143.6, 142.6, 142.2, 129.7, 128.7, 128.7, 128.0, 127.8, 126.6, 126.5, 122., 120.4, 110.4, 64.6, 64.1, 61.2, 55.5, 51.9, 51.0, 45.8, 42.1, 37.5 ppm.

IR ($CHCl_3$) λ3.332 (br), 1598, 188, 1449, 1254 $cm^{-1}$ (br).

EXAMPLE 13

(2SR, 3SR, 4RS)-2-Diphenylmethyl-3-methoxy-5-chlorophenyl)-methylamino]-4-(2-hydroxyethyl)pyrrolidine $^{13}C$ NMR ($CDCl_3$, 62.9 MHz) δ155.8, 143.6, 142.7, 129.9, 129.2, 128.7, 128.0, 127.8, 127.6, 126.6, 126.5, 125.1, 111.2, 64.5, 64.3, 61.2, 55.4, 51.9, 51.0, 46.0, 42.2, 37.5 ppm.

IR ($CHCl_3$) λ3338 (br), 2923, 1598, 1480, 1450 $cm^{-1}$.

EXAMPLE 14

(2SR, 3SR, 4RS)-2-Diphenylmethyl-3-[(2-methoxy-5-(1-methylethane)phenyl)methylamino]-4-(2-hydroxyethyl)pyrrolidine $^{13}C$ NMR ($CDCl_3$, 62.9 MHz) δ155.5, 143.7, 1431, 143.1, 140.6, 128.6, 128.6, 128.2, 128.1, 127.9, 127.6, 126.5, 126.4, 125.5, 110.0, 64.6, 61.5, 55.2, 51.6, 51.1, 47.1, 42.5, 37.3, 33.2, 24.2, 24.1 ppm.

EXAMPLE 15

(2SR, 3SR, 4RS)-2-Diphenylmethyl-3-[(2-methoxy-5-(1-methylpropane)phenyl)methylamino]-4-(2-hydroxyethyl)pyrrolidine $^{13}$C NMR (CDCl$_3$, 62.9 MHz) δ155.5, 143.7, 143.1, 139.4, 128.6, 128.6, 128.5, 128.2, 127.9, 126.4, 126.3, 126.2, 126.2, 110.0, 64.7, 64.6, 64.5, 61.5, 55.2, 51.6, 51.1, 47.1, 47.0, 42.0, 42.6, 40.7, 37.4, 31.3, 31.2, 22.0, 21.9, 12.2 ppm.

EXAMPLE 16

(2SR, 3SR, 4RS)-2-Diphenylmethyl-3-[(2-trifluoromethoxy-5-(1-dimethylethane)phenyl)methylamino]-4-(2-hydroxyethyl)pyrrolidine $^{13}$C NMR (CDCl$_3$, 62.9 MHz) δ149.7, 145.0, 143.6, 142.7, 131.8, 128.8, 128.7, 128.1, 127.8, 127.4, 126.6, 125.1, 120.0, 64.7, 64.6, 61.4, 52.1, 51.0, 45.9, 42.4, 37.4, 34.5, 31.4 ppm.

The title compounds of Examples 17–19 were prepared by the procedure described in Example 11B, starting from the appropriate aldehyde reagent of choice in each instance.

EXAMPLE 17

(2SR, 3SR, 4RS)-2-diphenylmethyl-3-[(2-methoxy-4,5-dimethylphenyl)methylamino]-4-(2-hydroxethyl)pyrrolidine $^1$H NMR (CDCl$_3$, 250 MHz) δ7.43–7.14 (m, 10H), 6.62 (s, H), 6.60 (s, 1H), 4.24–4.20 (d, 1H, J=9.8 Hz), 3.95–3.89 (dd, 1H, J=9.8 Hz, J=5.4 Hz), 3.71 (s, 3H), 3.59–3.47 (m, 4H), 3.28–3.21 (dd, 1H, J=10.1 Hz, J=8.3 Hz), 2.94–2.90 (t, 1H, J=4.9 Hz), 2.66 (br.s), 2.53–2.46 (dd, 1H, J=10.2 Hz), 2.23 (s, 3H), 2.14 (s, 3H), 2.11–2.06 (obsc. m, 1H), 1.66–1.58 (dd, 1H, J=13.0 Hz, J=6.5 Hz)ppm.

$^{13}$C NMR (CDCl$_3$, 62.9 MHz) δ155.3, 143.6, 142.9, 136.2, 131.1, 128.7, 128.6, 128.2, 127.9, 126.5, 126.4, 124.8, 112.0, 64.6, 64.5, 61.4, 55.3, 51.4, 51.1, 46.3, 42.3, 37.4, 20.0, 18.6 ppm.

HRMS calc'd for C$_{29}$H$_{36}$N$_2$O$_2$ 444.2777. Found 444.27856.

EXAMPLE 18

(2SR, 3SR, 4RS)-2-diphenylmethyl-3-[(2-trifluoromethoxyphenyl)methylamino]-4-(2-hydroxyethyl)pyrrolidine $^1$H NMR (CDCl$_3$, 300 MHz) δ7.47–7.03 (m, 13H), 6.90–6.87 (d, 1H, J=7.5 Hz), 4.23–4.19 (d, 1H, J=10.6 Hz), 3.91–3.85 (dd, 1H, J=10.6 Hz, J=5.1 Hz), 3.72–3.66 (d, 1H, J=14.4 Hz), 3.61–3.52 (m, 3H), 3.34–3.27 (t, H, J=9.7 Hz), 2.83–2.79 (t, 1H, J=4.7 Hz), 2.55–2.47 (dd, 1H, J=9.8 Hz, J=6.7 Hz), 2.24–2.17 (m, 1H), 2.1–1.8 (br.s), 1.67–1.59 (dd, 2H, J=13.4 Hz, J=6.7 Hz)ppm.

$^{13}$C NMR (CDCl$_3$, 75.5 MHz) δ147.1, 143.6, 142.7, 132.6, 129.8, 128.8, 128.3, 128.0, 127.9, 126.8, 126.6, 126.6, 120.3, 64.7, 63.6, 61.3, 52.1, 51.1, 44.5, 41.9, 37.5 ppm.

IR (CHCl$_3$) λ2918, 1598, 1482, 1449, 1244, 1163, 904 cm$^{-1}$.

HRMS FAB (p+1) calc'd for C$_{27}$H$_{29}$N$_2$O$_2$F$_3$ 471.2259. Found 471.2299.

EXAMPLE 19

(2SR, 3SR, 4RS)-2-diphenylmethyl-3-[(2-methyl-5-(1,1-dimethylethyl)phenyl)methylamino]-4-(2-hydroxyethyl)pyrrolidine $^1$H NMR (CDCl$_3$, 250 MHz) δ7.40–7.01 (m, 13H), 4.19–4.16 (d, 1H, J=10.6 Hz), 3.93–3.87 (dd, 1H, J=10.6 Hz), 3.93–3.87 (dd, 1H, J=10.6 Hz, J=5.2 Hz), 3.66–3.60 (m, 3H), 3.34–3.26 (dd, 2H, J=9.9 Hz, J=7.2 Hz), 2.95–2.91 (dd, 1H, J=5.0 Hz, J=3.8 Hz), 2.56–2.50 (dd, 1H, J=10.1 Hz, J=6.8 Hz), 2.28–2.23 (m, 1H), 2.07 (s, 3H), 1.91 (br.s), 1.75–1.65 (m, 2H), 1.30 (s, 9H) ppm.

$^{13}$C NMR (CDCl$_3$, 62.9 MHz) δ148.6, 143.7, 142.7, 137.5, 133.3, 129.9, 128.7, 128.7, 128.0, 127.9, 126.5, 125.8, 123.8, 65.0, 64.9, 61.4, 52.0, 51.2, 49.9, 42.2, 37.5, 34.3, 31.4, 18.2 ppm.

IR (CHCl$_3$) λ3686, 2946, 904 cm$^{-1}$.

HRMS calc'd for C$_{31}$H$_{40}$N$_2$O 456.31405. Found 456.3134.

EXAMPLE 20

(1SR, 2SR, 2SR, 4RS)-1-aza-2-diphenylmethyl-3-[(2-methoxy-4,5-dimethylphenyl)-methylamino]-bicyclo[2.2.1]heptane Title compound was prepared by a procedure similar to that of Examples 3D and 3E, except that 2-methoxy-4,5-dimethylbenzaldehyde (prepared according to the procedure described by W. E. Smith in the *Journal of Organic Chemistry*, Vol. 37, No. 24, p. 3972 (1972), starting from 3,4-dimethylanisole (Aldrich)) was employed as the starting material of choice in this particular instance.

Anal. calc'd for C$_{29}$H$_{34}$N$_2$O•2HCl•H$_2$O C: 67.30, H: 7.40, N: 5.41. Found C 66.9,5, H: 7.16, N: 5.18.

EXAMPLE 21

Resolution of (2SR, 3SR, 4RS)-2-diphenylmethyl-3-amino-3-(2-hydroxyethyl)pyrrolidine (2S, 3S, 4R)-2-diphenylmethyl-3-amino-4-(2-hydroxyethyl)pyrrolidine A solution of 0.750 gm (2.53 mmol) (2SR, 3SR, RS)-2-diphenylmethyl-3-amino-4-(2-hydroxyethyl)pyrrolidine (the product of Example 11A) and 0.978 gm (2.53 mmol) of di-p-toluoyl-D-tartaric acid (unnatural) was prepared with heating in 77 ml of methanol. The solution was concentrated to a volume of 25 ml by distillation at atmospheric pressure and allowed to stand for 18 hours at room temperature. At this point crystallization was underway. The mixture was concentrated further (by heating) to 20 ml and then allowed to cool. After 1 hour, the mixture was filtered to afford 210 mg of a salt with the following rotation [α]$_D^{20}$=+85.33° (c=0.3 g/100 ml). This material was set aside. The mother liquor was allowed to stand for 18 hours whereupon further crystallization occurred. This solid was washed with 5 ml of methanol and 25 ml of ether to yield 520 mg of a pale yellow solid {[α]$_D^{20}$=+23.89° (c=0.38 g/100 ml, MeOH)}. This material was recrystallized by dissolving the material in hot methanol (30 ml), concentrating to a volume of 20 ml, and allowing the solution to stand at room temperature. There was obtained 480 mg of pale yellow crystals {mp=163°–164° C.; [α]$_D^{20}$=+20.56° (c=0.32 g/100 ml, MeOH)}. An x-ray diffraction study of this tartarate salt as a single crystal confirmed the indicated (2S, 3S, 4R) stereochemistry.

A solution of 438 mg (0.64 mmol) of the above salt in 50 ml of methylene chloride was treated with 10 ml of 25% aqueous NaOH. The mixture was agitated and the organic phase was washed with brine, dried with sodium sulfate and evaporated in vacuo (190 mg). A portion of the residue was dissolved in methanol for rotation [α]$_D^{20}$=81.15° (C=0.33 g/100 ml).

The title compounds of Examples 22–24 were prepared using enantiomerically pure (2S, 3S, 4R)-2-diphenylmethyl-3-amino-4-(2-hydroxyethyl)pyrrolidine (prepared as indicated above) by following the procedure described in example 11B and employing the appropriate aldehyde reagent of choice as the key starting material in each instance.

EXAMPLE 22

(2S, 3S, 4R)-2-diphenylmethyl-3-[(2-methoxy-5-(1-methylethyl)phenyl)methylamino]-4-(2-hydroxyethyl)pyrrolidine•dihydrochloride Salt $^1$H NMR (D$_2$O, 250 MHz) δ7.40–7.26 (m, 11H), 6.92–6.90 (d, 1H, J=1.9 Hz), 6.82–6.78 (d, 1H, J=8.6 Hz), 5.02–4.95 (dd, 1H, J=12.5 Hz, J=5.7 Hz), 4.51–4.47 (d, 1H, J=12.4 Hz), 4.17–4.01 (q, 2H, J=13.4 Hz), 3.91–3.89 (br.d, 1H, J=5.7 Hz), 3.87–3.78 (dd, 1H, J=12.7 Hz, J=8.1 Hz), 3.66–3.50 (obsc. m, 2H), 3.59 (s, 3H), 3.24–3.16 (dd, 1H, J=12.8 Hz), 2.97–2.76 (m, 2H), 1.88–1.83 (m, 2H), 1.18–1.15 (dd, 6H, J=6.9 Hz) ppm.

$^{13}$C NMR (CDCl$_3$, 62.9 MHz) δ155.5, 143.7, 143.0, 140.6, 128.7, 128.6, 128.2, 128.1, 127.9, 127.6, 126.5, 126.4, 125.5, 109.9, 64.7, 64.6, 61.4, 5.2, 51.6, 51.1, 47.1, 42.5, 37.4, 33.2, 24.3, 24.2 ppm.

[α]$_D^{20}$=−17.53° (c=0.3 g/100 ml; MeOH)

EXAMPLE 23

(2S, 3S, 4R)- 2-diphenylmethyl-3-[(2-methoxy-4,5-dimethylphenyl)methylamino]-4-(2-hydroxyethyl)pyrrolidine Anal. calc'd for C$_{29}$H$_{36}$N$_2$O$_2$•2HCl•0.75 H$_2$O: C: 65.59, H: 7.50, N: 5.28. Found: C: 65.52, H: 7.52, N: 5.20.

[α]$_D^{20}$=−12.58° (C=0.76 g/100 ml; methanol). =.

EXAMPLE 24

(2S, 3S, 4R)-2-diphenylmethyl-3-[(2-methoxy-5-1,1-dimethylethyl)phenyl)methylamino-4 -(2-hydroxyethyl)pyrrolidine HRMS calc'd for C$_{31}$H$_{40}$N$_2$O$_2$: 472.3080. Found: 472.30901.

EXAMPLE 25

(2SR, 3SR, 4RS)-2-diphenylmethyl-3-[(2-methoxy-5-methylethyl)phenyl)methylamino-4-methylcarboxylpyrrolidine A. (2SR, 3SR, 4RS)-1N-phenylmethyl-2-diphenylmethyl-3-[(2-methoxy-5-(methylethyl)phenyl)methylamino-4-carbomethoxymethylpyrrolidine A solution of the intermediate prepared in example 1E, (2SR, 3SR, 4RS)-1N-phenylmethyl-2-diphenylmethyl-3-amino-4-carbomethoxymethylpyrrolidine, (606 mg, 1.46 mmol) in 100 ml of dichloroethane was treated with 261 mg (1.46 mmol) 2-methoxy-5-isopropylbenzaldehyde (prepared according to the procedure described by W. E. Smith in the *Journal of Organic Chemistry*, Vol. 37, No. 24, p. 3972 (1972), ultimately starting from 4-isopropylphenol (Aldrich)) and 465 mg (2.19 mmol) sodium triacetoxyborohydride. The reaction mixture was stirred for 18 hours and then quenched with saturated aqueous sodium borohydride. The mixture was extracted with methylene chloride, washed with brine, dried with sodium sulfate and evaporated. The residue was chromatographed on silica gel eluting with 10% ethyl acetate in hexane to afford 615 mg (62%) of an oil.

$^1$H NMR (CDCl$_3$, 300 MHZ) δ7.66–7.63 (d, 2H, J=1.2 HZ), 7.42–7.39 (d, 2H, J=7.2 HZ), 7.31–7.08 (m, 12H), 6.97–6.96 (d, 1H, J=2.3 Hz), 6 81–6 79 (d, 1H, J=8.4 Hz), 4.30–4.28 (d,, 1H, J=7.1 Hz), 3.82 (s, 3H), 3.75–3.68 (2H, m), 3.59 (S, 3H), 3.44–3.35 (t, 2H, J=12.9 Hz), 3.17–3.12 (dd, 1H, J=9.7 Hz, J=6.4 Hz), 3.06–3.02 (d, 1H, J=12.7 Hz), 2.94–2.85 (m, 2H), 2.56–2.50 (dd, 1H, J=14.5 Hz, J=4.1 Hz), 2.24–2.16 (m, 1H), 2.16–2.08 (dd, 1H, J=14.5 Hz, J=9.2 Hz), 1.98–1.92 (dd, H, J=9.6 Hz, J=8.2 Hz), 1.56 (br. s), 1.30–1.28 (d, 6H, J=6.9 Hz) ppm.

$^{13}$C NMR (CDCl$_3$, 75.5 MHz) δ173.2, 155.5, 144.2, 143.4, 140.8, 140.0, 129.7, 128.8, 128.6, 128.5, 128.3, 128.0, 126.6, 126.4, 125.9, 125.5, 110.1, 70.0, 66.1, 61.9, 57.8, 55.3, 52.9, 51.4, 48.0, 40.0, 37.6, 33.4, 24.4 ppm.

B. (2SR, 3SR, 4RS)-2-diphenylmethyl-3-[(2-methoxy-5-(methylethyl)phenyl)methylamino]-4-carbomethoxymethyl-pyrrolidine A sample of the compound prepared in step A (211 mg, 0.366 mmol) was dissolved in 30 ml of methanol (MeOH) and 30 ml of HCl$_g$-MeOH and treated with 36 mg of 10% palladiums on carbon (Pd/C). The mixture was placed under 50 psi hydrogen pressure for 3 hours. The reaction mixture was filtered through Celite®, washed with MeOH and the filtrate was stripped to a glass. Upon trituration of the residue with ether there was obtained 205 mg (100%) of the title compound as the hydrochloride salt.

$^1$H NMR (D$_2$O, 300 MHz) δ7.50–7.29 (m, 11H), 6.98 (s, 1H), 6.88–6.82 (d, 1H, J=7.9 Hz), 5.11–5.03 (dd, 1H, J=14.3 Hz, J=7.1 Hz), 4.8–4.7 (obsc., 1H), 4.57–4.53 (d, 1H, J=13.6 Hz), 4.22–4.08 (q, 2H, 14.2 Hz), 4.01–3.87 (m, 2H), 3.73 (s, 3H), 3.66 (s, 3H), 3.61–3.51 (m, 1H), 3.36–3.19 (m, 2H), 2.91–2.73 (m, 2H) , 1.21–1.18 (d, 6H, J=6.9 Hz) ppm.

C. (2SR, 3SR, 4RS)-2-diphenylmethyl-3-[(2-methoxy-5-(methylethyl)phenyl)methylamino]-4-methylcarboxylpyrrolidine The product from the previous step (Step B) (219 mg, 0.391 mmol) was taken up in 20 ml of water and THF (1:1) and treated with 99 mg (2.4 mmol) lithium hydroxidemonohydrate. The turbid reaction mixture was stirred for 6 hours. The mixture was adjusted to pH 6.9 with 1N hydrochloric acid and extracted with methylene chloride. The organic phase was dried with sodium sulfate and evaporated. The residue was chromatographed on silica gel (gradient 10%–20%–50% MeOH in methylene chloride) to afford 40 mg of the desired material.

Mass spectrum (FAB): 473 (p+1)

HRMS calc'd for $C_{30}H_{37}N_2O_3$ (m+1) 473.28041. Found: 473.2811.

EXAMPLE 26

(2SR, 3SR, 4RS)-2-diphenylmethyl-3-[(2-methoxy-5-(methylethyl)phenyl)methylamino]-4-(2-dimethylaminocarbamoyl-ethyl)pyrrolidine A. (2SR, 3SR, 4RS)-1N-phenylmethyl-2-diphenylmethyl-3-(1-dimethylethoxycarbonylamido)-4-(2-dimethylaminocarbamoylethyl)pyrrolidine The compound prepared in example 3A, (2SR, 3SR, 4RS)-1N-phenylmethyl-2-diphenylmethyl-3-(1,1-dimethylethoxycarbonylamido)-4-(2-hydroxyethyl)pyrrolidine, (417 mg, 0.857 mmol) was added to a solution of 108 mg (0.942 mmol) of 35% potassium hydride (in mineral oil) in 40 ml of THF kept at 0° C. The reaction mixture was stirred for 1 hour at this temperature and was then treated with 221 mg (2.05 mmol) of dimethylcarbamyl chloride. The reaction mixture was allowed to warm to room temperature and was stirred for 18 hours. The reaction mixture was treated with 40 ml of water and extracted with methylene chloride. The organic layer was washed with brine and then dried and evaporated. The residue was chromatographed on silica gel eluting with 30% ethyl acetate in hexane to afford 328 mg of the above titled product.

$^{13}$C NMR (CDCl$_3$, 62.9 MHZ) δ155.4, 155.3, 143.2, 142.6, 139.4, 130.0, 129.0, 128.7, 128.5, 128.3, 128.2, 128.0, 126.7, 126.6, 126.0, 79.2, 68.9, 64.1, 61.8, 58.4, 57.9, 53.5, 41.2, 36.3, 35.7, 32.6, 31.5, 28.4 ppm.

B. (2SR, 3SR, 4RS)-2-diphenylmethyl-3-amino-4-(2-dimethylaminocarbamoylethyl)pyrrolidine To a 250 ml Parr Bottle was charged 10 ml of methanol, mg of 10% palladium on carbon and a solution of 310 mg (0.55 mmol) (2SR, 3SR, 4RS)-1N-phenylmethyl-2-diphenylmethyl-3-(1,1-dimethylethoxycarbonylamido)-4-(2-dimethylaminocarbamoylethyl)pyrrolidine in 10 ml of methanol. The mixture was treated with 15 ml of methanol previously saturated with HCl gas. The hydrogenolysis was initiated at 50 psi hydrogen pressure and maintained at this pressure for 18 hours. The reaction mixture was then filtered through Celite® and evaporated in vacuo. The residue was partitioned between methylene chloride and 20% aqueous sodium hydroxide. The organic phase was washed with brine, dried with sodium sulfate and evaporated. The residue was used directly in the next step.

$^{1}$H NMR (CDCl$_3$, 250 MHz) δ7.3–7.13 (m, 10H), 4.11–4.01 (m, 3H), 3.68–3.62 (dd, 1H, J=11.0 Hz, J=4.9 Hz), 3.32–3.25 (dd, 1H, J=9.8 Hz, J=7.2 Hz), 3.00–2.97 (dd, 1H, J=4.8 Hz, J=2.1 Hz), 2.87 (s, 3H), 2.82 (s, H), 2.45–2.38 (dd, 1H, J=9.9 Hz, J=6.9 Hz), 1.90–1.68 (m, 2H) ppm.

$^{13}$C NMR (CDCl$_3$, 62.9 MHz) δ156.6, 143.6, 142.3, 128.9, 8.7, 127.9, 127.8, 126.7, 126.5, 65.9, 64.1, 57.8, 52.4, 51.6, 46.2, 36.4, 35.8, 33.4 ppm.

C. (2SR, 3SR, 4RS)-2-diphenylmethyl-3-[(2-methoxy-5-(methylethyl)phenyl)methylamino]-4-(2-dimethylaminocarbamoylethyl)pyrrolidine A solution of 100 mg (0.272 mmol) [(2SR, 3SR, 4RS)-2-diphenylmethyl-3-amino-4-(2-dimethylaminocarbamoylethyl)pyrrolidine](the product of Example 26B) in 25 ml of dichloroethane was treated with 48 mg (0.272 mmol) of 2-methoxy-5isopropylbenzaldehyde and 81 mg (0.381 mmol) of sodium triacetoxyborohydride. The reaction mixture was stirred for 18 hours and then quenched with 15 ml of saturated aqueous sodium bicarbonate. The reaction mixture was extracted with methylene chloride and the organic phase was washed with brine, dried and evaporated. The residue was chromatographed on silica gel eluting with 97/2/1 (methylene chloride/methanol/ammonia) to afford 89 mg (62%) of the title compound.

$^{13}$C NMR (CDCl$_3$, 62.9 MHz) δ156.6, 155.6, 144.0, 142.7, 0.5, 128.7, 128.5, 127.9, 126.4, 125.4, 109.9, 65.6, 64.2, 63.9, 55.2, 51.8, 51.6, 46.9, 42.3, 36.4, 35.8, 34.0, 33.2,

Anal. calc'd for $C_{33}H_{43}N_3O_3$•HCl•1.5H$_2$O: C: 62.95, H: 7.68, N: 6.67. Found: C: 63.18, H: 7.44, N: 6.59.

EXAMPLE 27

(2SR, 3SR, 4RS)-2-diphenylmethyl-3-[(2-methoxy-5-(1-methylethyl)phenyl)methylamino]-4-(2-methoxyethyl)pyrrolidine A. (2SR, 3SR, 4RS)-1N-phenylmethyl-2-diphenylmethyl-3-(1,1-dimethylethoxycarbonylamido)-4-(2-methoxyethyl)pyrrolidine The compound prepared in example 3A, (2SR, 3SR, 4RS)-1N-phenylmethyl-2-diphenylmethyl-3-(1,1-dimethylethoxycarbonylamido)-4-(2-hydroxyethyl)pyrrolidine, (405 mg, 0.83 mmol) was added to a solution of 105 mg (0.92 mmol) of 35% potassium hydride (in mineral oil) containing 284 mg (2.0 mmol) methyl iodide in 8 ml of THF kept at 0° C. The reaction mixture wets stirred for 18 hours while warming to room temperature. The reaction mixture, now containing a precipitate, was treated with 10 ml of water and extracted with methylene chloride. The organic layer was washed with brine and then dried and evaporated. The residue was chromatographed on silica gel eluting first with 98:1:1 (methylene chloride: methanol: ammonia) followed by 94:5:1 to afford 375 mg of the above title compound.

$^{13}$C NMR (CDCl$_3$, 62.9 MHz) δ155.1, 143.4, 142.9, 139.5, 129.7, 128.6, 128.5, 128.3, 128.1, 128.0, 126.6, 126.5, 125.9, 70.9, 68.7, 61.6, 58.4, 58.2, 58.0, 53.8, 40.7, 32.2, 28.3 ppm.

B. (2SR, 3SR, 4RS)-2-diphenylmethyl-3-amino-4-(2-methoxyethyl)pyrrolidine

To a 250 ml Parr Bottle was charged 10 ml of methanol, 38 mg of 10% palladium on carbon and a solution of 375 mg (0.55 mmol) (2SR, 3SR, 4RS)-1N-phenylmethyl-2-diphenylmethyl-3-(1,1-dimethylethoxycarbonylamido)-4-(2-methoxyethyl)pyrrolidine (prepared as described above) in 10 ml of methanol. The mixture was treated with 25 ml of methanol previously saturated with HCl gas. The hydrogenolysis was initiated at 50 psi hydrogen pressure and maintained at this pressure for 18 hours. The reaction mixture was then filtered through Celite® and evaporated in vacuo. The residue was partitioned between methylene chloride and 20% aqueous sodium hydroxide. The organic phase was washed with brine, dried with sodium sulfate and evaporated. The residue (213 mg) was used directly in the next step.

$^{13}$C NMR (CDCl$_3$, 62.9 MHz) δ143.7, 142.4, 128.8, 128.7, 128.6, 127.9, 127.8, 126.6, 126.4, 71.4, 65.8, 58.6, 57.9, 52.5, 51.5, 46.1, 33.9 ppm.

C. (2SR, 3SR, 4RS)-2-diphenylmethyl-3-[(2-methoxy-5-(1-methylethyl)phenyl)methylamino]-4-(2-methoxyethyl)pyrrolidine A solution of 109 mg (0.35 mmol) of [(2SR, 3SR, 4RS)-2-diphenylmethyl-3-amino-4-(2-methoxyethyl)pyrrolidine] (the product of Example 27B) in 35 ml of dichloroethane was treated with 63 mg (0.35 mmol) of 2-methoxy-5-isopropylbenzaldehyde and 104 mg (0.49 mmol) of sodium triacetoxyborohydride. The reaction mixture was stirred for 18 hours and then quenched with 30 ml of saturated aqueous sodium bicarbonate. The reaction mixture was extracted with methylene chloride and the organic phase was washed with brine, dried and evaporated. The residue was chromatographed on silica gel eluting with 97/2/1 (methylene chloride/methanol/ammonia) to afford 102 mg (62%) of the title compound.

$^{13}$C NMR (CDCl$_3$, 62.9 MHz) δ155.5, 143.9, 142.7, 140.5, 128.6, 128.5, 128.0, 127.9, 127.9, 126.4, 125.3, 109.9, 71.3, 65.4, 63.7, 58.5, 55.2, 51.5, 51.3, 46.9, 42.0, 34.5, 33.2, 24.3, 24.2 ppm.

EXAMPLE 28

2SR, 3SR, 4RS)-2-diphenylmethyl-3-[(2-methoxy-5-(1,1-dimethylethyl)phenyl)methylamino]-4-(2-methoxyethyl)pyrrolidine The title compound was prepared according to the procedure of Example 27, except that 2-methoxy-5-(1,1-dimethylethyl)benzaldehyde was the starting material of choice employed instead of the corresponding 5-isopropyl compound.

We claim:
1. A compound of the formula:

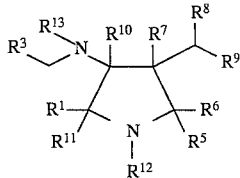

(I)

or a pharmaceutically acceptable salt thereof, wherein $R^1$ is phenyl or benzhydryl which is diphenylmethyl;

$R^3$ is 2-methoxyphenyl, 2-trifluoromethoxyphenyl, 2-methoxy-5-trifluoromethoxyphenyl, 2-methoxy-5-chlorophenyl, 2-methoxy-5-(1-methylethyl)phenyl, 2-methoxy-5-(1-methyl-n-propyl)phenyl, 2-methoxy-5-(1,1-dimethylethyl)phenyl, 2-methoxy-4,5-dimethylphenyl or 2-methyl-5-(1,1-dimethylethyl)phenyl;

$R^5$, $R^6$, $R^7$, $R^8$, $R^{10}$, $R^{11}$, $R^{12}$ and $R^{13}$ are each hydrogen;

$R^9$, when separately, is carboxy, hydroxymethyl, methoxymethyl or N,N-dimethylaminocarbamoyl; and $R^9$, when taken together with the carbon atom to which it is attached, the nitrogen atom of the pyrrolidine ring, the carbon atom to which $R^7$ is attached and the carbon atom to which $R^5$ and $R^6$ are each attached, completes a second pyrrolidine ring, thereby forming a bicyclic ring structure containing a bridgehead nitrogen atom in the ring, with the proviso that R12 is always absent.

2. A compound according to claim 1, wherein $R^1$ is benzhydryl.

3. A compound according to claim 1, wherein said compound is selected from the group consisting of:

(1SR, 2SR, 3SR, 4RS)-1-aza-2-diphenylmethyl-3-[(2-methoxyphenyl)methylamino]bicyclo[2.2.1]heptane;

(1SR, 2SR, 3SR, 4RS)-1-aza-2-diphenylmethyl-3-[(2-methoxy-5-(1,1-dimethylethyl)phenyl)methylamino]bicyclo[2.2.1]heptane;

(1SR, 2SR, 3SR, 4RS)-1-aza-2-diphenylmethyl-3-[(2-methoxy-5-trifluoromethoxyphenyl)methylamino]bicyclo2.2.1]heptane;

(1SR, 2SR, 3SR, 4RS)-1-aza-2-diphenylmethyl-3-[(2-methoxy-5-(1-methylethyl)phenyl)methylamino]bicyclo2.2.1]heptane;

(1SR, 2SR, 3SR, 4RS)-1-aza-2-diphenylmethyl-3-[(2-methoxy-5-propylphenyl)methylamino]bicyclo[2.2.1]heptane;

(1SR, 2SR, 3SR, 4RS)-1-aza-2-diphenylmethyl-3-[(2-methoxy-5-(1-methylpropyl)phenyl)methylamino]bicyclo[2.2.1]heptane;

(1SR, 2SR, 3SR, 4RS)-1-aza-2-phenyl-3-[(2-methoxyphenyl)methylamino]bicyclo[2.2.1]heptane;

(1SR, 2SR, 3RS, 4RS)-1-aza-2-phenyl-3-[(2-methoxy-5-trifluoromethoxyphenyl)methylamino]bicyclo[2.2.1]heptane;

(2SR, 3SR, 4RS)-N-1-phenylmethyl-2-diphenylmethyl-3-(2-methoxyphenyl)methylamino]-4-(2-hydroxyethyl)pyrrolidine;

(2SR, 3SR, 4RS)-2-diphenylmethyl-3-[(2-methoxyphenyl)methylamino]-4-(2-hydroxyethyl)pyrrolidine;

(2SR, 3SR, 4RS)-2-diphenylmethyl-3-[(2-methoxy-5-(1,1-dimethylethyl)phenyl)methylamino]-4-(2-hydroxyethyl)pyrrolidine;

(2SR, 3SR, 4RS)-2-diphenylmethyl-3-[(2-methoxy-5-trifluoromethoxyphenyl)methylamino]-4-(2-hydroxyethyl)pyrrolidine;

(2SR, 3SR, 4RS)-2-diphenylmethyl-3-[(2-methoxy-5-(1-methylethyl)phenyl-2-methylamino]-4-(2-hydroxyethyl)pyrrolidine;

(2SR, 3SR, 4RS)-2-diphenylmethyl-3-[(2-methoxy-5-propylphenyl)methylamino]-4-(2-hydroxyethyl)pyrrolidine;

(2SR, 3SR, 4RS)-2-diphenylmethyl-3-[(2-methoxy-5-(1-methyl-1-propyl)phenyl)methylamino]-4-(2-hydroxyethyl)pyrrolidine;

(2SR, 3SR, 4RS)-2-diphenylmethyl-3-[(2-trifluoromethoxy-5-(1,1-dimethylethyl)phenyl)methylamino]-4-(2-hydroxyethyl)pyrrolidine;

(2SR, 3SR, 4RS)-2-diphenylmethyl-3-[(2-methoxy-5-chlorophenyl)methylamino]-4-(2-hydroxyethyl)pyrrolidine;

(2SR, 3SR, 4RS)-2-phenyl-3-[(2-methoxyphenyl)methylamino]-4-(2-hydroxyethyl)pyrrolidine;

(2SR, 3SR, 4RS)-2-diphenylmethyl-3-[(2-methoxy-4,5-dimethylphenyl)methylamino]-4-(2-hydroxyethyl)pyrrolidine;

(2SR, 3SR, 4RS)-2-diphenylmethyl-3-[(2-methoxy-4,5-dimethylphenyl)methylamino]-4-(2-hydroxyethyl)pyrrolidine;

(2SR, 3SR, 4RS)-2-diphenylmethyl-3-[(2-methoxy-5-(methylethyl)phenyl)methylamino]-4-(carbomethoxymethyl)pyrrolidine;

(2SR, 3SR, 4RS)-2-diphenylmethyl-3-[(2-methoxy-5-(methylethyl)phenyl)methylamino]-4-(carboxymethyl)pyrrolidine;

(2SR, 3SR, 4RS)-2-diphenylmethyl-3-[(2-methoxy-5-(methylethyl)phenyl)methylamino]-4-(2-dimethylaminocarbamoylethyl)pyrrolidine;

(2SR, 3SR, 4RS)-2-diphenylmethyl-3-[(2-trifluoromethoxyphenyl)methylamino]-4-(2-hydroxyethyl)pyrrolidine;

(2S, 3S, 4R)-2-diphenylmethyl-3-[(2-methoxy-5-(1,1-dimethylethyl)phenyl)methylamino]-4-(2-hydroxyethyl)pyrrolidine;

(2SR, 3SR, 4RS)-2-diphenylmethyl-3-[(2-methoxy-5-(1,1-dimethylethyl)phenyl)methylamino]-4-(2-methoxyethyl)pyrrolidine;

(2S, 3S, 4R)-2-diphenylmethyl-3-[(2-methoxy-5-methylethyl)phenyl)methylamino]-4-(2-hydroxyethyl)pyrrolidine;

(2SR, 3SR, 4RS)-2-diphenylmethyl-3-[(2-methoxy-5-methylethyl)phenyl)methylamino]-4-(2-methoxyethyl)pyrrolidine;

(2SR, 3SR, 4RS)-2-diphenylmethyl-3-[(2-methyl-5-(1,1-dimethylethyl)phenyl)methylamino]-4-(2-hydroxyethyl)pyrrolidine;

(1SR, 2SR, 3SR, 4RS)-1-aza-2-diphenylmethyl-3-[(2-methoxy-4,5-dimethylphenyl)methylamino]-bicyclo[2.2.1]heptane;

(2SR, 3SR, 4RS)-2-phenyl-3-[(2-methoxy-5-(1,1-dimethylethyl)phenyl)methylamino]-4-(2-hydroxyethyl)pyrrolidine; and (2SR, 3SR, 4RS)-2-phenyl-3-[(2-methoxy-5-trifluoromethoxyphenyl)methylamino]-4-(2-hydroxyethyl)pyrrolidine.

4. A compound according to claim 1, wherein said compound is 2-diphenylmethyl-3-[(2-methoxyphenyl)methylamino]-4-(2-hydroxyethyl)pyrrolidine.

5. A compound according to claim 1, wherein $R^1$ is diphenylmethyl; $R^9$, when taken separately, is carboxy, hydroxymethyl, methoxymethyl or N,N-dimethylaminocarbamoyl, and $R^{12}$ is hydrogen.

6. A compound according to claim 1, wherein $R^1$ is phenyl; $R^9$, when taken separately, is carboxy, hydroxymethyl, methoxymethyl or N,N-dimethylaminocarbamoyl, and $R^{12}$ is hydrogen.

7. A compound according to claim 1, wherein $R^1$ is diphenylmethyl; $R^9$, when taken together with the carbon atom to which it is attached, the nitrogen atom of the pyrrolidine ring, the carbon atom to which $R^7$ is attached and the carbon atom to which $R^5$ and $R^6$ are each attached, completes a second pyrrolidine ring, thereby forming a bicyclic ring structure containing a bridgehead nitrogen atom in the ring, with the proviso that $R^{12}$ is always absent.

8. A compound according to claim 5, having the formula (I), wherein $R^1$ is diphenylmethyl, $R^3$ is 2-methoxyphenyl, $R^9$ is hydroxymethyl, and $R^5$, $R^6$, $R^7$, $R^8$, $R^{10}$, $R^{11}$, $R^{12}$ and $R^{13}$ are each hydrogen, which is (2SR, 3SR, 4RS)-2-diphenylmethyl-3-[(2-methoxyphenyl)methylamino]-4-(2-hydroxyethyl)pyrrolidine.

9. An antipsychotic pharmaceutical composition comprising an effective substance P receptor antagonist amount of a compound as claimed in claim 1 and a pharmaceutically acceptable carrier therefor.

10. A method of antagonizing the effects of substance P in a mammal, comprising administering to said mammal a substance P antagonizing effective amount of a compound according to claim 1.

11. A pharmaceutical composition for treating or preventing a condition in a mammal, the treatment or prevention of which is effected or facilitated by a decrease amount of a compound according to claim 1 effective in antagonizing the effect of substance P at its receptor site and a pharmaceutically acceptable carrier.

12. A method of treating or preventing a condition in a mammal, the treatment or prevention of which is effected or facilitated by a decrease in substance P mediated neurotransmission, comprising administering to a mammal in need of such treatment or prevention an amount of a compound according to claim 1, or a pharmaceutically acceptable salt thereof, effective in antagonizing the effect of substance P at its receptor site.

* * * * *